(12) United States Patent
Wong et al.

(10) Patent No.: US 6,312,888 B1
(45) Date of Patent: Nov. 6, 2001

(54) DIAGNOSTIC ASSAY FOR A SAMPLE OF BIOLOGICAL FLUID

(75) Inventors: Sie Ting Wong, Mundelein, IL (US); Robert G. Hiltibran, Bristol, WI (US); Tung-Ming Huang, Buffalo Grove, IL (US); Brenda B. Calfin, Chicago, IL (US); Mark R. Pope, Grayslake, IL (US); Thomas G. Schapira, Bristol, WI (US); Eric B. Shain, Glencoe, IL (US); Douglas F. Young, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/688,636

(22) Filed: Oct. 16, 2000

Related U.S. Application Data

(63) Continuation of application No. 09/241,183, filed on Feb. 1, 1999, which is a continuation-in-part of application No. 09/095,270, filed on Jun. 10, 1998.

(51) Int. Cl.$^7$ ...................................................... C12Q 1/00
(52) U.S. Cl. ............................................ 435/4; 435/283.1
(58) Field of Search ..................................... 435/4, 283.1

(56) References Cited

U.S. PATENT DOCUMENTS

| | | | |
|---|---|---|---|
| 3,690,836 | 9/1972 | Buissiere et al. | 435/4 |
| 4,088,448 | 5/1978 | Lilja et al. | 435/4 |
| 4,233,029 | 11/1980 | Columbus | 435/4 |
| 4,254,083 | 3/1981 | Columbus | 435/4 |
| 4,255,384 | 3/1981 | Kitajima et al. | 435/4 |
| 4,255,788 | 3/1981 | Schwartz et al. | 435/4 |
| 4,256,693 | 3/1981 | Kondo et al. | 435/4 |
| 4,258,001 | 3/1981 | Pierce et al. | 435/4 |
| 4,292,272 | 9/1981 | Kitajima et al. | 435/4 |
| 4,298,345 | 11/1981 | Sodickson et al. | 435/4 |
| 4,323,536 | 4/1982 | Columbus | 435/4 |
| 4,420,566 | 12/1983 | Jessop et al. | 435/4 |
| 4,452,887 | 6/1984 | Kitajima et al. | 435/4 |
| 4,552,458 | 11/1985 | Lowne | 435/4 |
| 4,685,059 | 8/1987 | Yamamoto | 435/4 |
| 4,772,561 | 9/1988 | Genshaw | 435/4 |

(List continued on next page.)

FOREIGN PATENT DOCUMENTS

| | | |
|---|---|---|
| 0 215 419 | 3/1987 | (EP) . |
| 0 487 068 | 5/1992 | (EP) . |
| 0 977 032 | 2/2000 | (EP) . |

*Primary Examiner*—Louise N. Leary
(74) *Attorney, Agent, or Firm*—David L. Weinstein

(57) ABSTRACT

An article and a method for monitoring the concentration of an analyte, e. g., glucose, in blood. In one aspect, the invention involves an article comprising a multiple-layer element. In one embodiment, the article comprises:

a multiple-layer element comprising:
(a) a base layer
(b) a cover layer, the cover layer having a first opening for venting the multiple-layer element and a second opening for receiving a biological sample; and
(c) a core layer having a first major surface and a second major surface, the core layer disposed between the base layer and the cover layer, the core layer comprising a sample introduction chamber and a optical reading chamber, the first major surface of the core layer in face-to-face contact with the base layer, the second major surface of the core layer in face-to-face contact with the cover layer.

The multiple-layer element of this invention allows the use of samples of blood or other biological fluids, such as interstitial fluid, to provide extremely sensitive assay results. The device has been shown to provide accurate and reproducible results with samples having volumes ranging from about 5 $\mu$L to about 20 $\mu$L. In another aspect, the invention involves a method for using the aforementioned article.

37 Claims, 18 Drawing Sheets

U.S. PATENT DOCUMENTS

| | | | |
|---|---|---|---|
| 4,774,192 | 9/1988 | Terminiello et al. | 435/4 |
| 4,810,470 | 3/1989 | Burkhardt et al. | 435/4 |
| 4,849,340 | 7/1989 | Oberhardt | 435/4 |
| 4,895,704 | 1/1990 | Arai et al. | 435/4 |
| 4,902,629 | 2/1990 | Meserol et al. | 435/4 |
| 4,935,346 | 6/1990 | Phillips et al. | 435/4 |
| 5,049,487 | 9/1991 | Phillips et al. | 435/4 |
| 5,059,394 | 10/1991 | Phillips et al. | 435/4 |
| 5,104,811 | 4/1992 | Berger et al. | 435/4 |
| 5,147,606 | 9/1992 | Charlton et al | 435/4 |
| 5,179,005 | 1/1993 | Phillips et al. | 435/4 |
| 5,271,895 | 12/1993 | McCroskey et al. | 435/4 |
| 5,278,047 | 1/1994 | Lilja et al. | 435/4 |
| 5,304,467 | 4/1994 | Sakamoto et al. | 435/4 |
| 5,304,468 | 4/1994 | Phillips et al. | 435/4 |
| 5,409,664 | 4/1995 | Allen | 435/4 |
| 5,426,032 | 6/1995 | Phillips et al. | 435/4 |
| 5,563,042 | 10/1996 | Phillips et al | 435/4 |
| 5,681,529 | 10/1997 | Taguchi et al. | 435/4 |
| 5,986,754 | 11/1999 | Harding | 356/246 |

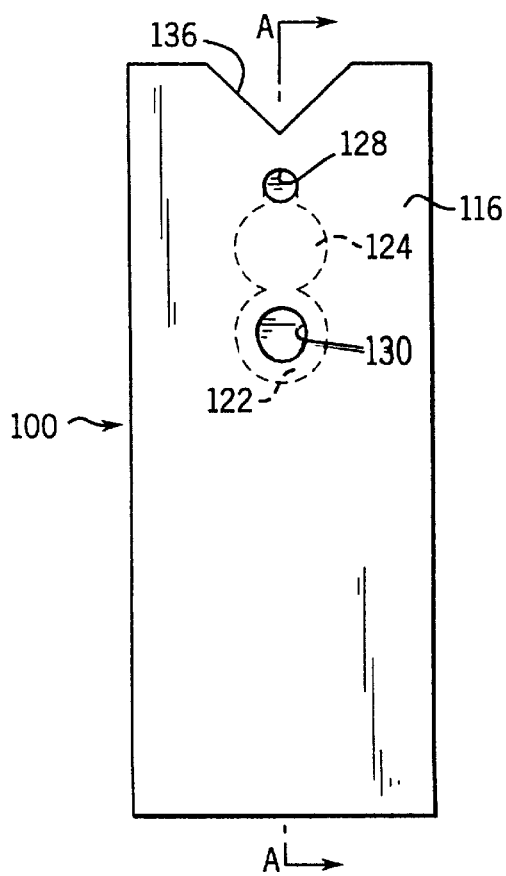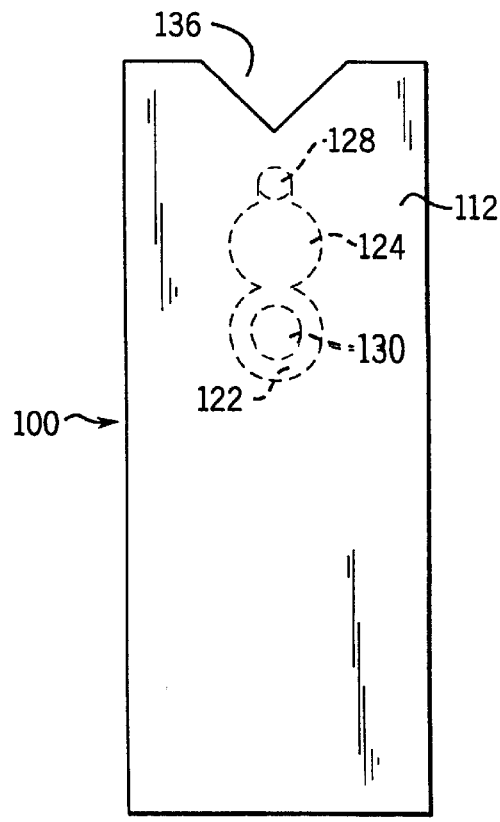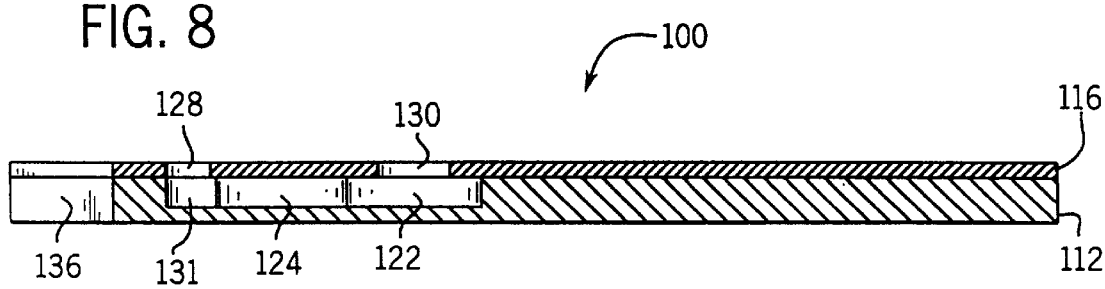

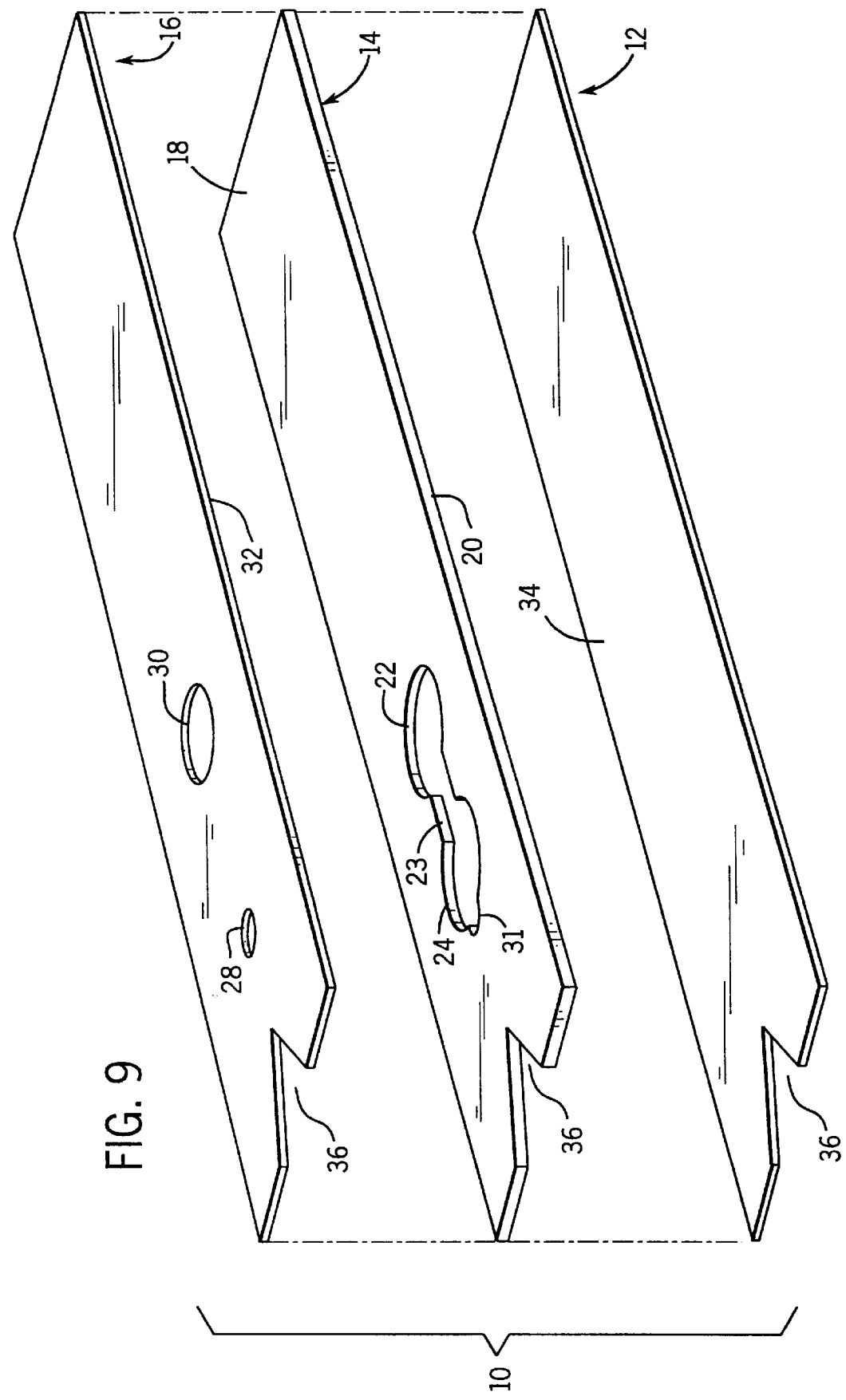

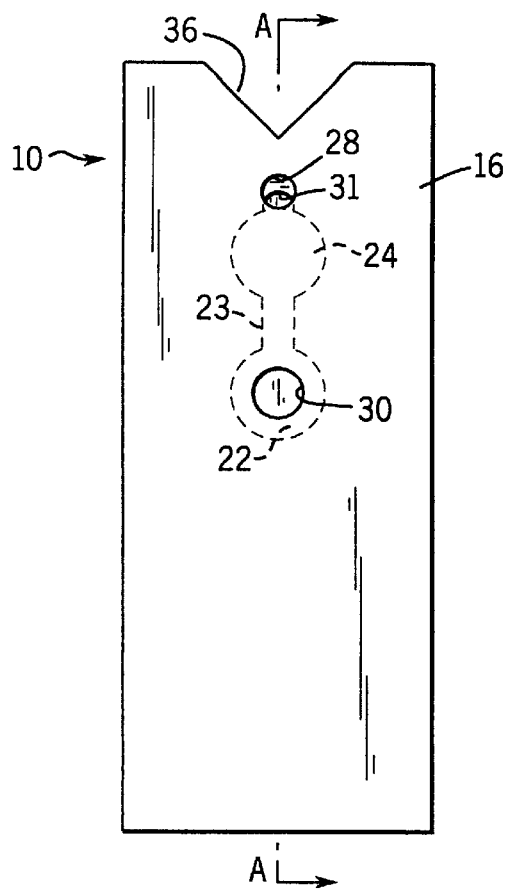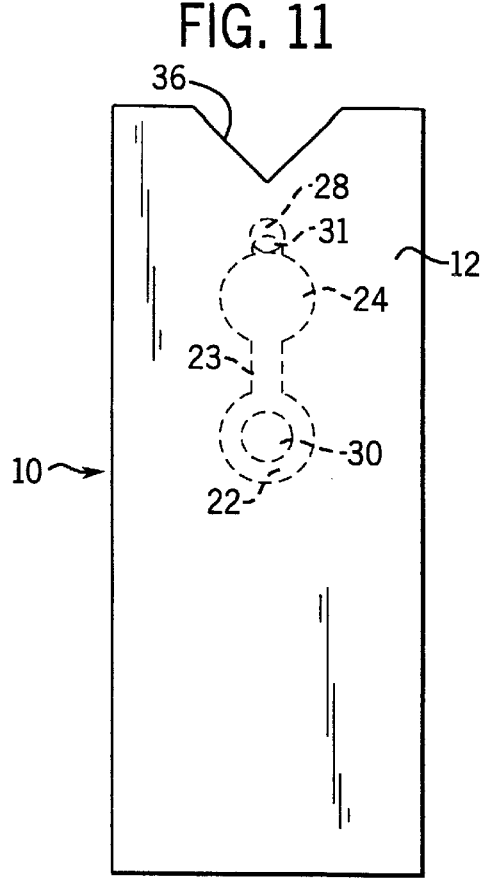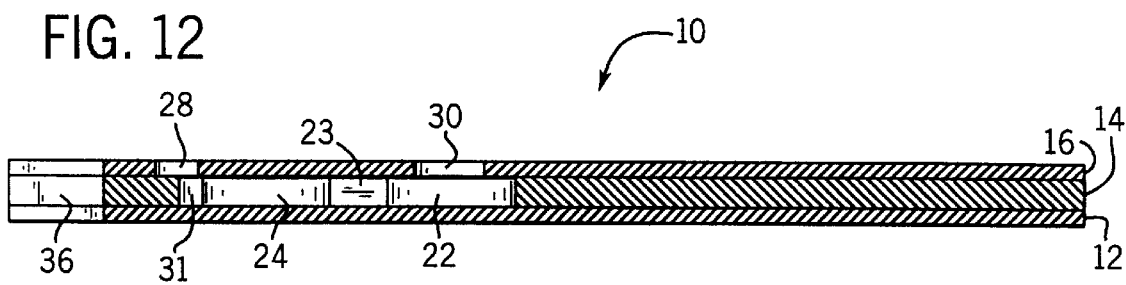

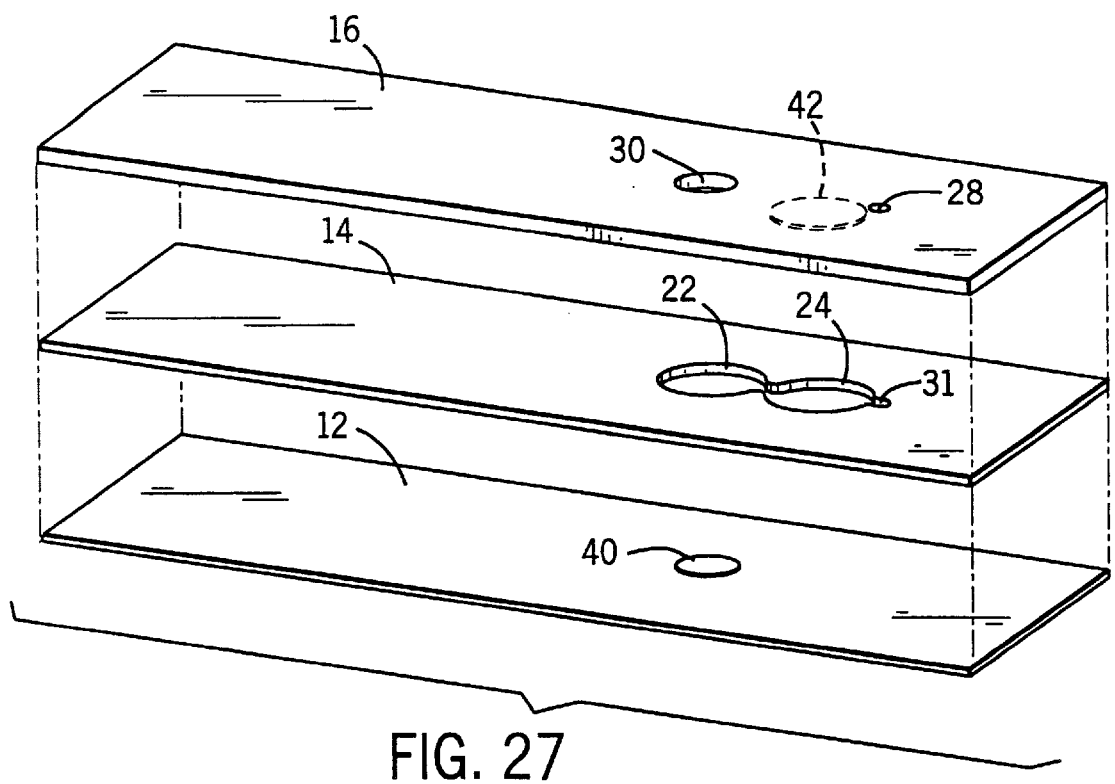
FIG. 27
FIG. 28
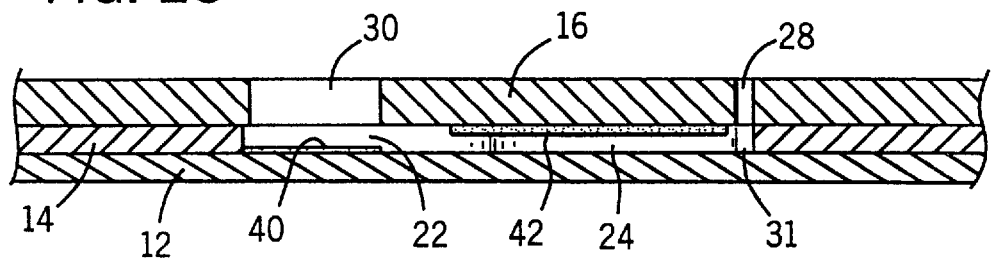

DIAGNOSTIC ASSAY FOR A SAMPLE OF BIOLOGICAL FLUID

This application is a con of Ser. No. 09/241,183, filed Feb. 1, 1999 which is a continuation-in-part of U.S. Ser. No. 09/095,270, filed Jun. 10, 1998.

BACKGROUND OF THE INVENTION

1. Field of the Invention

This invention relates to the field of monitoring the amount of an analyte, e. g., glucose, cholesterol, in body fluid. More particularly, this invention provides an article and method that monitors the amount of analyte in body fluid by means of a reagent that reacts with the analyte in the body fluid.

2. Discussion of the Art

The prevalence of diabetes has been increasing markedly in the world. At this time, diagnosed diabetics represented about 3% of the population of the United States. It is believed that the total actual number of diabetics in the United States is over 16,000,000. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse many of the effects of diabetes.

Glucose monitoring devices of the prior art have operated on the principle of first taking a sample of blood from an individual by any of a variety of methods, such as by needle or lancet. The individual then inserts a strip carrying reagents into a blood glucose meter in which glucose concentration is determined by a change in reflectance. The individual then applies the sample of blood to the strip. The blood reacts with the reagents and causes a change in reflectance of the strip, thereby indicating the concentration of glucose in the sample of blood. There are numerous devices currently available for diabetics to monitor the concentration of glucose in blood.

One of these devices is the "LIFESCAN" glucose meter. This glucose meter is sold under the tradenames "ONE TOUCH PROFILE" and "ONE TOUCH BASIC." This glucose meter and products associated therewith are described in U.S. Pat. Nos. 4,935,346; 5,304,468; 5,426,032; 5,563,042; 5,049,487; 5,059,394; 5,179,005, all of which are incorporated herein by reference. This glucose meter uses optical detection technology and a mixture of reagents comprising glucose oxidase, horse radish peroxidase, and color-generating materials known as chromogens. The reagents are located on "ONE TOUCH" reagent-carrying test strips. These devices suffer from the shortcoming of interference from serum components, which adversely affect the accuracy of glucose readings. The glucose oxidase reagent system suffers interference from such materials as bilirubin and ascorbic acid, both of which are always present in the blood in substantial amounts. Another shortcoming of these devices is that the blood applied to the "ONE TOUCH" test strip often migrates to the bottom surface of the "ONE TOUCH" test strip. The blood then transfers onto the glucose meter, and, as a result, users are required to clean the glucose meter after each use. Otherwise, residual blood remaining on the glucose meter will have a detrimental effect on the performance of the glucose meter or on the optical measuring component thereof.

In view of the aforementioned shortcomings, it would be desirable to provide a test strip having a reagent system that resists the effects of such blood components as bilirubin and ascorbic acid. It would also be desirable to provide a test strip that would minimize the migration of blood from the test strip to the glucose meter.

SUMMARY OF THE INVENTION

This invention provides an article and a method for monitoring the concentration of an analyte, e. g., glucose, in blood. In one aspect, the invention involves an article comprising an element having a plurality of layers, i. e., a multiple-layer element. In one embodiment, the article comprises:

a multiple-layer element comprising:
  (a) a base layer
  (b) a cover layer, the cover layer having a first opening for venting the multiple-layer element and a second opening for receiving a biological sample; and
  (c) a core layer having a first major surface and a second major surface, the core layer disposed between the base layer and the cover layer, the core layer comprising a sample introduction chamber and a optical reading chamber, the first major surface of the core layer in face-to-face contact with the base layer, the second major surface of the core layer in face-to-face contact with the cover layer.

The opening for receiving the biological sample communicates with the sample introduction chamber. The opening for venting communicates with a vent channel, which, in turn, communicates with the optical reading chamber. The optical reading chamber and the sample introduction chamber can be adjacent to one another or the optical reading chamber and the sample introduction chamber can be separated from one another but connected by means of a flow channel. Alternatively, the optical reading chamber and the sample introduction chamber can be combined, so long as the size of the combined chambers is sufficiently great that the sample is not introduced directly into the optical reading chamber.

Reagents that are capable of reacting with the analyte to form a reaction product that can be read by an optical instrument to provide the value of concentration of the analyte in the sample are located in the optical reading chamber. When the analyte is glucose, the reagents preferably comprise at least one enzyme and at least one dye. The device is capable of providing a determination of concentration of analyte in a meter designed for colorimetric measurements, such as, for example, the "LIFESCAN" "ONE TOUCH" devices, in about 45 seconds.

The multiple-layer element of this invention allows the use of samples of blood or other biological fluids, such as interstitial fluid, to provide extremely sensitive assay results. The device has been shown to provide accurate and reproducible results with samples having volumes ranging from about 5 $\mu$L to about 20 $\mu$L.

In another embodiment, the article comprises a multiple-layer element comprising:
  (a) a cover layer, the cover layer having a first opening for venting the multiple-layer element and a second opening for receiving a sample of biological fluid;
  (b) a base layer having a major surface in contact with the cover layer; and
  (c) a sample introduction chamber and an optical reading chamber formed in either the cover layer, the base layer, or both the cover layer and the base layer.

The opening for receiving the biological sample communicates with the sample introduction chamber. The opening for venting communicates with a vent channel, which, in turn, communicates with the optical reading chamber. The sample introduction chamber and the optical reading chamber can be adjacent to one another or the sample introduction chamber and the optical reading chamber can separated from one another but connected by means of a flow channel. Alternatively, the optical reading chamber and the sample introduction chamber can be combined, so long as the size of the combined chambers is sufficiently great that the sample is not introduced directly into the optical reading chamber.

The invention also provides means for determining when the optical reading chamber contains a sufficient volume of sample for allowing an accurate reading of an enzymatic reaction. One means involves a colorant that is introduced into the optical reading chamber from the sample introduction chamber or some other location in the element upstream of the optical reading chamber. The colorant would be dissolved or dispersed by the sample as the sample flows through the element. The sample containing the colorant would then be transported to the optical reading chamber where a reading would indicate a change in the optical property of the optical path of the optical reading chamber to indicate that the optical reading chamber contains the sample. The reading from the optical reading chamber can also be used to indicate when a sufficient volume of sample is present for a determination of concentration of an analyte. Another means involves a highly reflective coating overlying and aligned with the optical path of the optical reading chamber, which provides an initial reflectance reading prior to the introduction of the sample to the optical reading chamber. When the sample is introduced to the optical reading chamber, the highly reflective coating is washed away or dissolved by the sample, thereby producing a change in the reading from the optical reading chamber. The magnitude of this change can be employed to indicate when a sufficient volume of sample is present for a determination of concentration of an analyte. Another means involves a highly reflective, wettable, porous, hydrophilic membrane overlying and aligned with the optical path of the optical reading chamber. This membrane will effectively reflect light from a source of light. When the sample is introduced into the optical reading chamber, the membrane will be rapidly wetted and become translucent, thereby producing a change in the reading from the optical reading chamber. The magnitude of this change can be employed to indicate when a sufficient volume of sample is present for a determination of concentration of an analyte.

In another aspect, the invention involves a method for determining the concentration of an analyte in a biological sample comprising the steps of:

(a) introducing the biological sample obtained from the body of a patient, e. g., blood, to an article comprising a multiple-layer element having a sample introduction chamber and an optical reading chamber;

(b) allowing a reagent in the article to react with the analyte of interest in the sample; and (c) measuring the concentration of analyte in the sample by means of an optical instrument.

The preferred reagent comprises an enzyme that can react in an environment having a limited supply of oxygen. An example of such an enzyme is glucose dehydrogenase.

The article and method of this invention provide numerous advantages. The article allows for extremely accurate control of volume of sample. Even if the volume of the sample exceeds the volume required for the determination of the concentration of analyte, the article is unaffected by the excess volume of sample. Red blood cells can be present in the optical reading chamber without adversely affecting the accuracy of the reading. Blood lysate can be used in the article and method of the invention. The use of lysate reduces optical interference by providing a homogeneous sample for testing. The employment of a vent allows the article to prevent air lock, which would result in air bubbles and yield false readings. Blood samples having a high hematocrit do not affect the time required to provide a result. The article is designed so that blood cannot leak through it, thereby reducing the likelihood of contaminating the meter. The article is designed so that evaporation of sample is minimized and the effects of humidity are minimized.

BRIEF DESCRIPTION OF THE DRAWINGS

FIG. 6 is a top plan view of the article shown in FIG. 5.

FIG. 7 is a bottom plan view of the article shown in FIG. 5.

FIG. 8 is a view in cross-section taken along line A—A in FIG. 6.

FIG. 9 is an exploded perspective view of a article suitable for use in this invention. The article is similar to that shown in FIG. 1, with the exception being the positioning of the sample introduction chamber and the optical reading chamber.

FIG. 10 is a top plan view of the article shown in FIG. 9. The article is similar to that shown in FIG. 2, with the exception being the positioning of the sample introduction chamber and the optical reading chamber.

FIG. 11 is a bottom plan view of the article shown in FIG. 9. The article is similar to that shown in FIG. 3, with the exception being the positioning of the sample introduction chamber and the optical reading chamber.

FIG. 12 is a view in cross-section taken along line A—A in FIG. 10. The article is similar to that shown in FIG. 4, with the exception being the positioning of the sample introduction chamber and the optical reading chamber.

FIG. 27 is an exploded perspective view of a multiple-layer element showing the deposition of a light-absorbing colorant at the base of the sample introduction chamber. In this element, the liquid sample dissolves or disperses the colorant and resulting solution or dispersion is transported into the optical reading chamber, which contains the dried reagent.

FIG. 28 is a cross-sectional view corresponding to FIG. 27, showing the vent opening, the sample introduction site opening, the sample introduction chamber, and the optical reading chamber.

DETAILED DESCRIPTION

Figure 1:
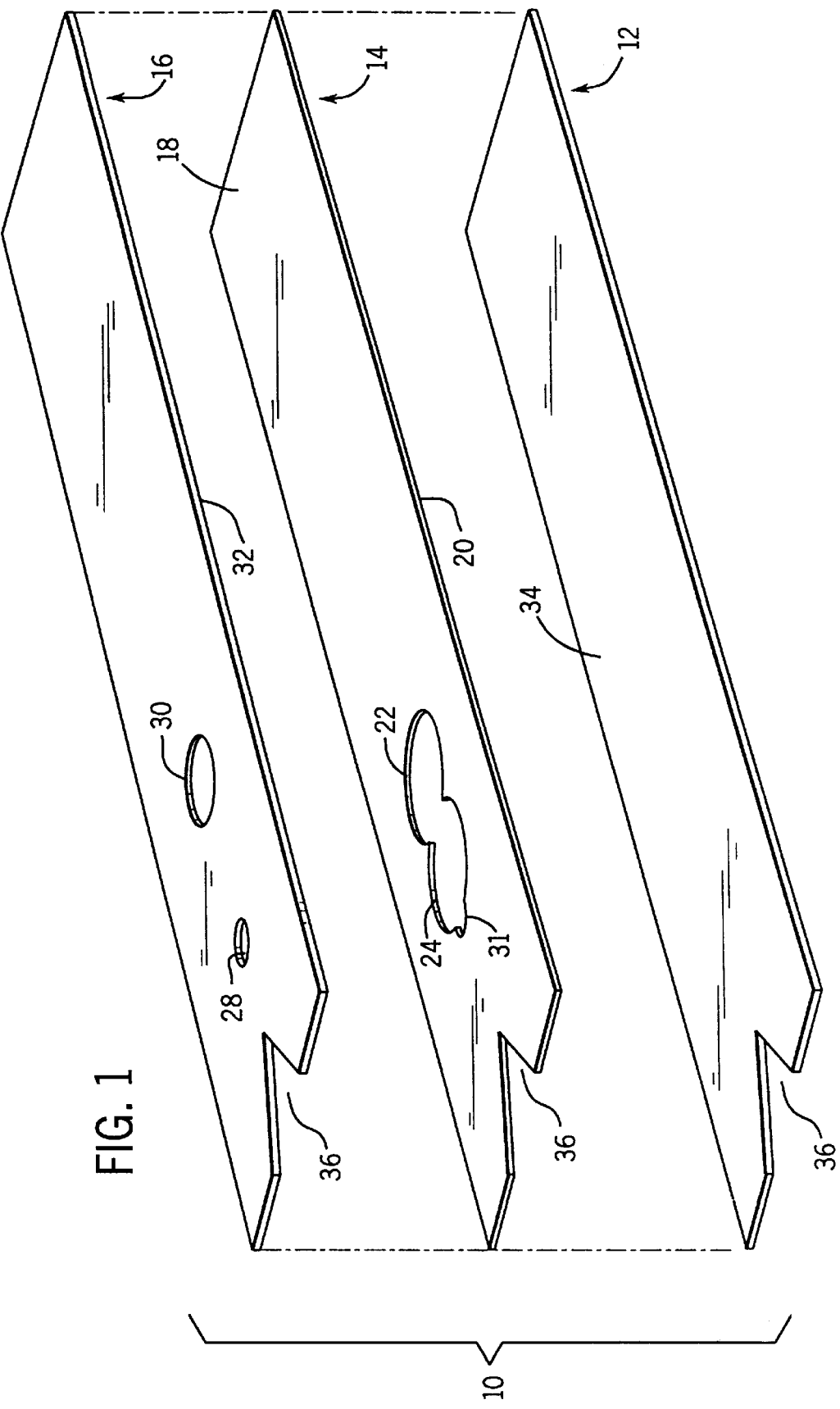
FIG. 1 is an exploded perspective view of a article suitable for use in this invention.
Figure 2:
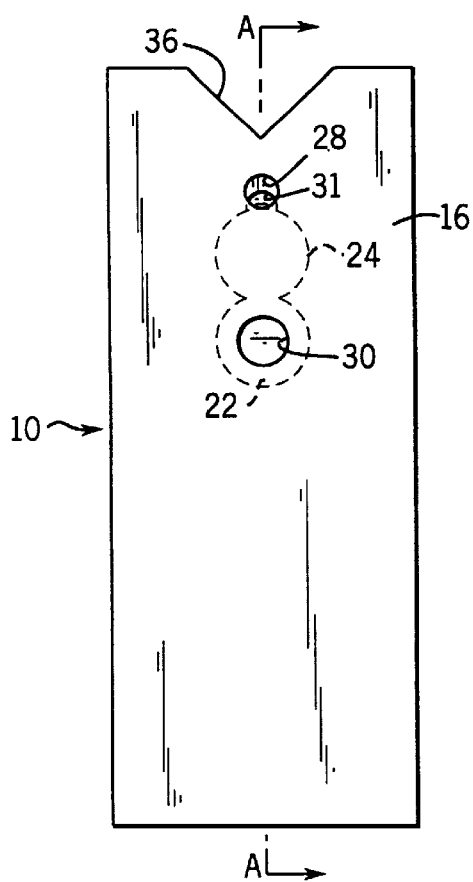
FIG. 2 is a top plan view of the article shown in FIG. 1.
Figure 3:
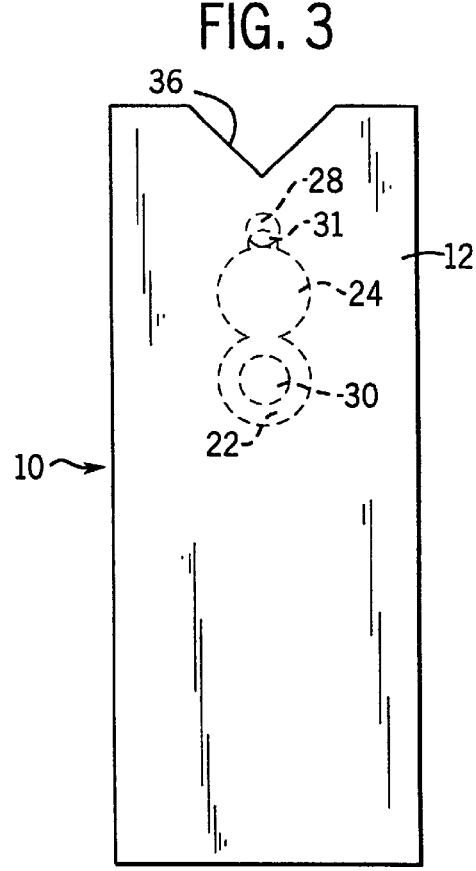
FIG. 3 is a bottom plan view of the article shown in FIG. 1.
Figure 4:
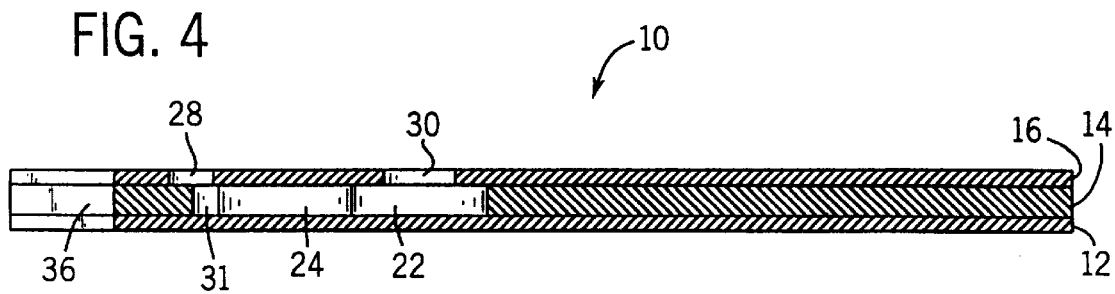
FIG. 4 is a view in cross-section taken along line A—A in FIG. 2.
Figure 5:
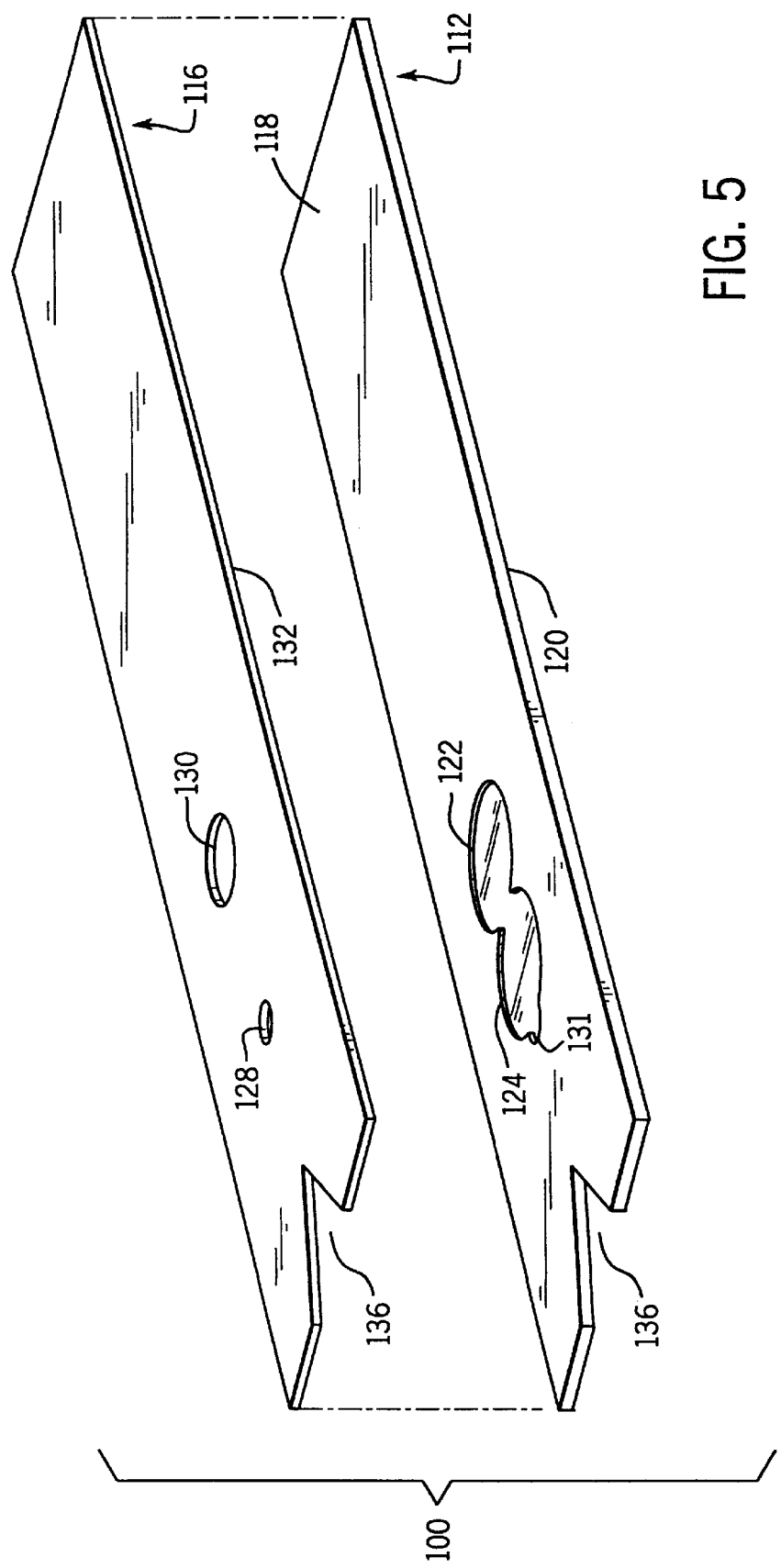
FIG. 5 is an exploded perspective view of a article suitable for use in this invention.
Figure 13:
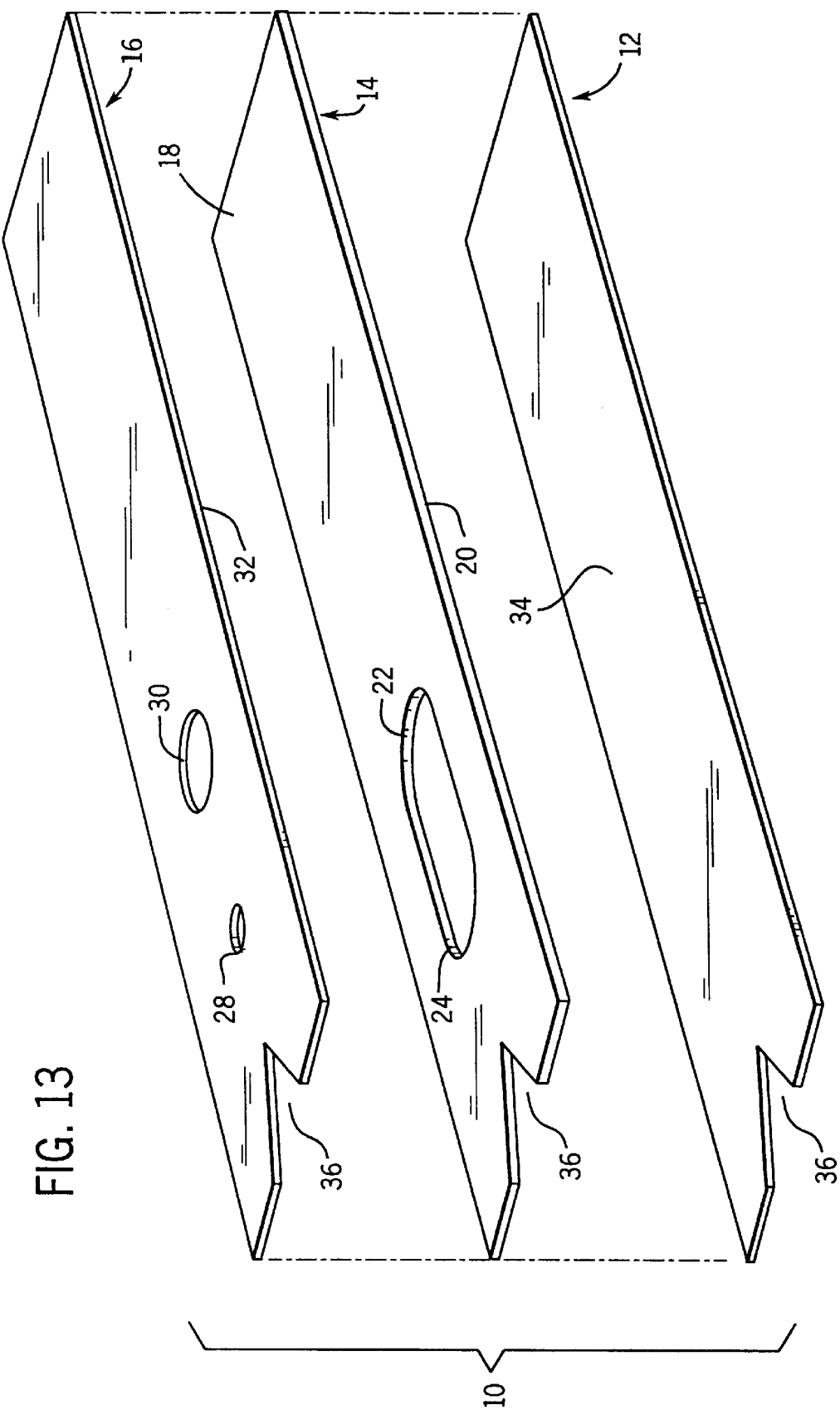
FIG. 13 is an exploded perspective view of a article suitable for use in this invention. The article is similar to that shown in FIG. 1, with the exception being the positioning of the sample introduction chamber and the optical reading chamber.
Figure 14:
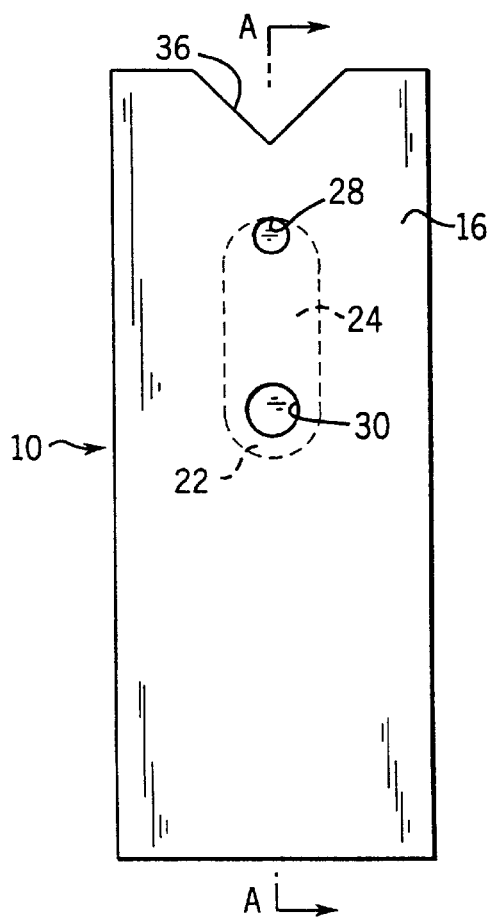
FIG. 14 is a top plan view of the article shown in FIG. 13. The article is similar to that shown in FIG. 2, with the exception being the positioning of the sample introduction chamber and the optical reading chamber.
Figure 15:
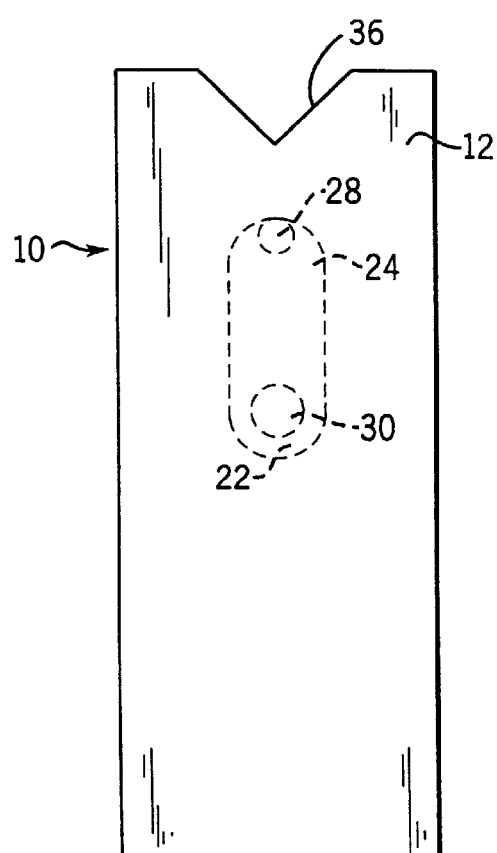
FIG. 15 is a bottom plan view of the article shown in FIG. 13. The article is similar to that shown in FIG. 3, with the exception being the positioning of the sample introduction chamber and the optical reading chamber.
Figure 16:
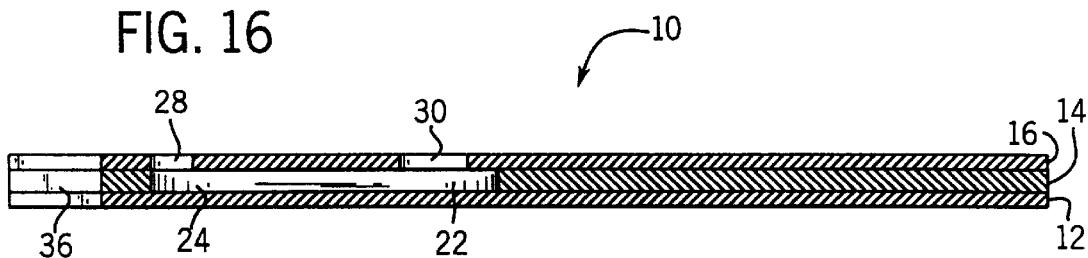
FIG. 16 is a view in cross-section taken along line A—A in FIG. 14. The article is similar to that shown in FIG. 4, with the exception being the positioning of the sample introduction chamber and the optical reading chamber.

As used herein, the expressions "reagent", "reagent composition", and the like, means one or more substances used in a chemical reaction to detect, examine, measure, or produce other substances. The expression "optical path" means the path traversed by the incident light that enters and travels through the optical reading chamber.

Referring now to FIGS. 1, 2, 3, and 4, the article 10 is a multiple-layer element comprising a base layer 12, a core layer 14 overlying the base layer 12, and a cover layer 16 overlying the core layer 14. The core layer 14 has a first major surface 18 and a second major surface 20. The core layer 14 comprises a sample introduction chamber 22 and an optical reading chamber 24. As shown in FIGS. 1, 2, 3, and 4, the sample introduction chamber 22 and the optical reading chamber 24 are adjacent to each other. Alternatively, the sample introduction chamber and the optical reading chamber can be spaced apart from each other and can be connected by a flow channel. The cover layer 16 has a first opening 28, which serves as a vent, and a second opening 30, which serves as a sample introduction site. The first opening 28 communicates with a vent channel 31. The second opening 30 communicates with the sample introduction chamber 22. This embodiment requires a base layer 12 below the core layer 14, because the sample introduction chamber 22 and the optical reading chamber 24 extend all the way through the core layer 14. A first major surface 32 of the cover layer 16 is in face-to-face contact with the first major surface 18 of the core layer 14. A first major surface 34 of the base layer 12 is in face-to-face contact with the second major surface 20 of the core layer 14. A notch 36 can be formed in one end of the article 10. The purpose of the notch 36 is to aid in positioning the article 10 in a glucose meter to align the optical reading chamber 24 with the source of light.

Referring now to FIGS. 5, 6, 7, and 8, the article 100 comprises a base layer 112 and a cover layer 116 overlying the base layer 112. The base layer 112 has a first major surface 118 and a second major surface 120. The base layer 112 comprises a sample introduction chamber 122 and an optical reading chamber 124. As shown in FIGS. 5, 6, 7, and 8, the sample introduction chamber 122 and the optical reading chamber 124 are adjacent to each other. Alternatively, the sample introduction chamber and the optical reading chamber can be spaced apart from each other and can be connected by a flow channel. The cover layer 116 has a first opening 128, which serves as a vent, and a second opening 130, which serves as a sample introduction site. The first opening 128 communicates with a vent channel 131. The second opening 130 communicates with the sample introduction chamber 122. A first major surface 132 of the cover layer 116 is in face-to-face contact with the first major surface 118 of the base layer 112. This embodiment does not require a third layer in face-to-face contact with the second major surface 120 of the base layer 112, because the sample introduction chamber 122 and the optical reading chamber 124 are recessed from the major surface 118 of the base layer 112. A notch 136 can be formed in one end of the article 100.

The purpose of the notch 136 is to aid in positioning the article 100 in a glucose meter to align the optical reading chamber 124 with the source of light. The embodiment shown in FIGS. 1, 2, 3, and 4 is preferred because it is easier to prepare in mass quantities.

In the description that follows, it can be assumed that a given component of the embodiment shown in FIGS. 5, 6, 7, 8, 9, 10, 11, 12, 13, 14, 15, and 16 is substantially similar to that same component shown in FIGS. 1, 2, 3, and 4, unless indicated otherwise. For example, the sample introduction chamber 122 of FIGS. 5, 6, 7, and 8 is substantially similar to the sample introduction chamber 22 of FIGS. 1, 2, 3, and 4.

Regardless of which embodiment is used, the surface dimensions of each layer are not critical, except to the extent that the dimensions must be selected so that the article will properly fit into the desired optical metering device. An example of surface dimensions suitable for a multiple-layer element of this invention are a length of 30 mm and a width of 20 mm. With respect to the preferred embodiment, as shown in FIGS. 1, 2, 3, and 4, the depth of the core layer 14 must be sufficient to accommodate the depth of the deeper of the sample introduction chamber 22 or the optical reading chamber 24. With respect to the preferred embodiment, as shown in FIGS. 1, 2, 3, and 4, representative examples of the thickness of the core layer 14 of the multiple-layer element range from 0.025 mm to 0.15 mm. The thickness of the base layer 12 of the multiple-layer element typically ranges from about 0.1 mm to about 0.3 mm. Representative examples of the thickness of the base layer 12 of the multiple-layer element are 0.15 mm and 0.25 mm. The thickness of the cover layer 16 of the multiple-layer element typically ranges from about 0.1 mm to about 0.3 mm. Representative examples of the thickness of the cover layer 16 of the multiple-layer element are 0.1 mm and 0.25 mm. Representative examples of dimensions of other features of the preferred embodiment as shown in FIGS. 1, 2, 3, and 4 are as follows:

TABLE I

| Feature | Dimensions |
| --- | --- |
| Sample introduction chamber | 4.77 mm diameter × 0.075 mm in depth |
| Optical reading chamber | 4.77 mm diameter × 0.075 mm in depth |
| Vent channel | 0.5 mm in the flow direction × 0.5 mm in width × 0.075 mm in depth |
| Sample introduction site | 2.8 mm diameter |
| Vent | 1.5 mm diameter |

Regardless of which embodiment is used, the dimensions of the sample introduction chamber and the optical reading chamber are not critical. However, the optical reading chamber must be of proper size to contain the required quantity of sample. The dimensions of the vent channel must be such that the vent channel does not consume an excessive quantity of the sample. The vent channel can have any shape. The diameter of the opening that serves as the vent must not be so great that the sample exits therefrom, with the result that an excessive quantity of sample is required. It is necessary that the vent channel and the opening that serves as the vent be outside both the path of the incident light entering the optical reading chamber and the path of the reflected light exiting the optical reading chamber, so that reflectance readings will not be adversely affected.

Each of the named layers, i. e., the base layer, the core layer, and the cover layer, can comprise a single layer of material or, in the alternative, two or more layers of material joined together, as by adhesive, heat sealing, or some other means of lamination.

A representative example of the volume of the optical reading chamber is 1.3 μL. A representative example of the volume of the sample introduction chamber is 1.3 μL. In general, the volume of the optical reading chamber is based on the area of the beam of light used for optical reading and the thickness of the layer in which the chambers are located.

In the embodiment of FIGS. 1, 2, 3, and 4, the portion of the cover layer 16 in register with the optical reading chamber is preferably sufficiently optically reflective so that at least about 75%, more preferably at least about 85%, most preferably at least about 90% of the incident light from the source of light of the optical instrument is reflected from the cover layer. Similarly, in the embodiment shown in FIGS. 5, 6, 7, and 8, the portion of the cover layer 116 in register with the optical reading chamber is preferably sufficiently optically reflective so that at least about 75%, more preferably at least about 85%, most preferably at least about 90% of the incident light from the source of light of the optical instrument is reflected from the cover layer. For ease of manufacture for any embodiment, it is preferred that the entire surface of the cover layer 116 facing the base layer 112 (FIGS. 5, 6, 7, and 8) be made of a single material; likewise, it is preferred that the entire surface of the cover layer 16 facing the core layer 14 (FIGS. 1, 2, 3, and 4) be made of a single material. In any of the embodiments, the portion of the base layer in register with the optical reading chamber should be made of a material that does not optically interfere with the optical reading. The material of the base layer should preferably not interfere with light reflected from the cover layer. For ease of manufacture for any embodiment, it is preferred that the entire base layer be made of a single material.

It is preferred that the base layer be capable of enhancing the transport of fluid from the sample introduction chamber to the optical reading chamber. The base layer can be coated with a surfactant to enhance the flow of fluid from the sample introduction chamber to the optical reading chamber. A representative example of a surfactant suitable for this function is a block-copolymer having the trademark "PLURONIC L-64".

It is necessary that the multiple-layer article have both a sample introduction chamber and an optical reading chamber. The reason for this requirement is that the sample cannot be introduced directly into the optical reading chamber because the surface of the cover must be capable of reflecting light. If an opening for introducing the sample to the article were placed in the cover layer in a region directly over the optical reading chamber, the cover layer in this region would not be capable of reflecting light.

There are several suitable ways of locating the sample introduction chamber and the optical reading chamber in the core layer of the embodiment of FIGS. 1, 2, 3, and 4 or in the base layer of the embodiment of FIGS. 5, 6, 7, and 8. In the most preferred embodiment, the optical reading chamber is located adjacent to the sample introduction chamber, as shown in FIGS. 1, 2, 3, and 4. When the sample introduction chamber and the optical reading chamber are adjacent, the region where the sample introduction chamber and the optical reading chamber have a common boundary is preferably sufficiently wide so that the rate of flow of fluid from the sample introduction chamber to the optical reading chamber is great enough that an analyte determination can be carried out in a reasonable time. FIGS. 9, 10, 11, and 12 illustrate an embodiment of a multiple-layer element in which the sample introduction chamber and the optical reading chamber are separated from one another but connected by a flow channel 23. The dimensions of the flow channel, if employed, must be such that the rate of flow through the flow channel does not unduly prolong the time required to make a determination of concentration of analyte. Representative examples of suitable dimensions for the optional flow channel are 0.5 mm in the flow direction by 0.5 mm in width by 0.075 mm in depth. FIGS. 13, 14, 15, and 16 illustrate an embodiment of a multiple-layer element in which the sample introduction chamber and the optical reading chamber are combined into a dual-purpose chamber. Where the sample introduction chamber and the optical reading chamber are combined into a dual-purpose chamber, the opening for introducing the sample into the sample introduction chamber portion of the dual purpose chamber must not be in the path of light that enters or exits the optical reading chamber portion of the dual purpose chamber, so that the light will be properly reflected from the surface of the cover layer. The remaining components of the multiple-layer elements in FIGS. 9, 10, 11, 12, 13, 14, 15, and 16, i. e., the base layer 12, the core layer 14, the cover layer 16, the vent opening 28, the sample introduction site opening 30, and the vent channel 31, and the notch 36 perform the same functions as those components having the same reference numerals in FIGS. 1, 2, 3, and 4. Regardless of which embodiment is used, the closer that the sample introduction chamber is to the optical reading chamber, the lower the volume of sample required. If the sample introduction chamber is placed at too great a distance from the optical reading chamber or if the cross-sectional area of the flow channel, if used, is excessively small, the flow rate of the sample will be reduced, and accordingly, increase the time required to obtain a result.

It is preferred that the sample introduction chamber be cylindrical or substantially cylindrical in shape; however, other shapes can also be employed. A cylindrical shape is preferred because it allows the use of a smaller volume of sample. The depth of the sample introduction chamber preferably ranges from about 0.025 mm to about 0.15 mm. It is preferred that the optical reading chamber be cylindrical or substantially cylindrical in shape; however, other shapes can also be employed. A cylindrical shape is preferred because such a shape conforms best to the optical interrogation pattern and allows the use of a smaller volume of sample. The depth of the optical reading chamber preferably ranges from about 0.025 mm to about 0.15 mm. Because of the requirement of sufficient width of the common boundary between the sample introduction chamber and the optical reading chamber when the chambers are adjacent, as shown in FIGS. 1, 2, 3, and 4, the optical reading chamber and the sample introduction chamber are not perfectly cylindrical but are merely substantially cylindrical.

If a flow channel joins the sample introduction chamber to the optical reading chamber, as shown in FIGS. 9, 10, 11, and 12, it is preferred that the rate of flow through the channel be sufficiently high that the duration of the assay is not unduly increased. It is preferred that the flow channel be coated with a surfactant, e. g., a block-copolymer having the trademark "PLURONIC L-64". It is also preferred that the flow channel be free of material that would obstruct the flow of the sample.

It is preferred that the duration of flow from the sample introduction chamber to the optical reading chamber not exceed 15 seconds, more preferably 10 seconds, most preferably 5 seconds.

The sample introduction chamber can contain a colorant, i. e., a dye or a pigment. The purpose of this colorant is to indicate when the optical reading chamber contains a sufficient amount of sample for the determination of the concentration of an analyte, because an insufficient amount of sample will lead to an inaccurate result. If a colorant is used, it can be deposited on the base layer, preferably in register with the sample introduction chamber. FIGS. 27 and 28 illustrate an embodiment of a multiple-layer element in which a colorant is deposited on the base layer in register with the sample introduction chamber. The colorant deposit is represented by the reference numeral 40. Alternatively, the colorant can be deposited on the base layer, but not in register with the sample introduction chamber. The colorant must not be deposited in the optical path of the optical reading chamber. The remaining components of the multiple-layer element in FIGS. 27 and 28, i. e., the base layer 12, the core layer 14, the cover layer 16, the sample introduction chamber 22, the optical reading chamber 24, the vent opening 28, the sample introduction site opening 30, and the vent channel 31, perform the same functions as those components having the same reference numerals in FIGS. 1, 2, 3, and 4. Upon addition of the sample to the sample introduction chamber, the colorant is dissolved, if a dye, or dispersed, if a pigment. When the colorant-containing sample reaches the optical reading chamber, the meter can measure the optical change induced by the colorant and begin the determination of the concentration of analyte. The colorant must be soluble or dispersible in the sample. The amount of colorant must be sufficient to provide an optical change measurable by an optical instrument. The particular amount of colorant depends upon the particular colorant and the dimensions of the component parts of the multiple-layer element. One skilled in the art is capable of determining the amount of colorant by trial and error without undue experimentation. The colorant can be selected to absorb light in the ultraviolet, the visible, or the infrared region of the electromagnetic spectrum. It is preferred that the colorant be able to absorb light having a wavelength in the range of from about 350 nm to about 1400 nm, more preferably from about 350 nm to about 700 nm.

Figure 29:
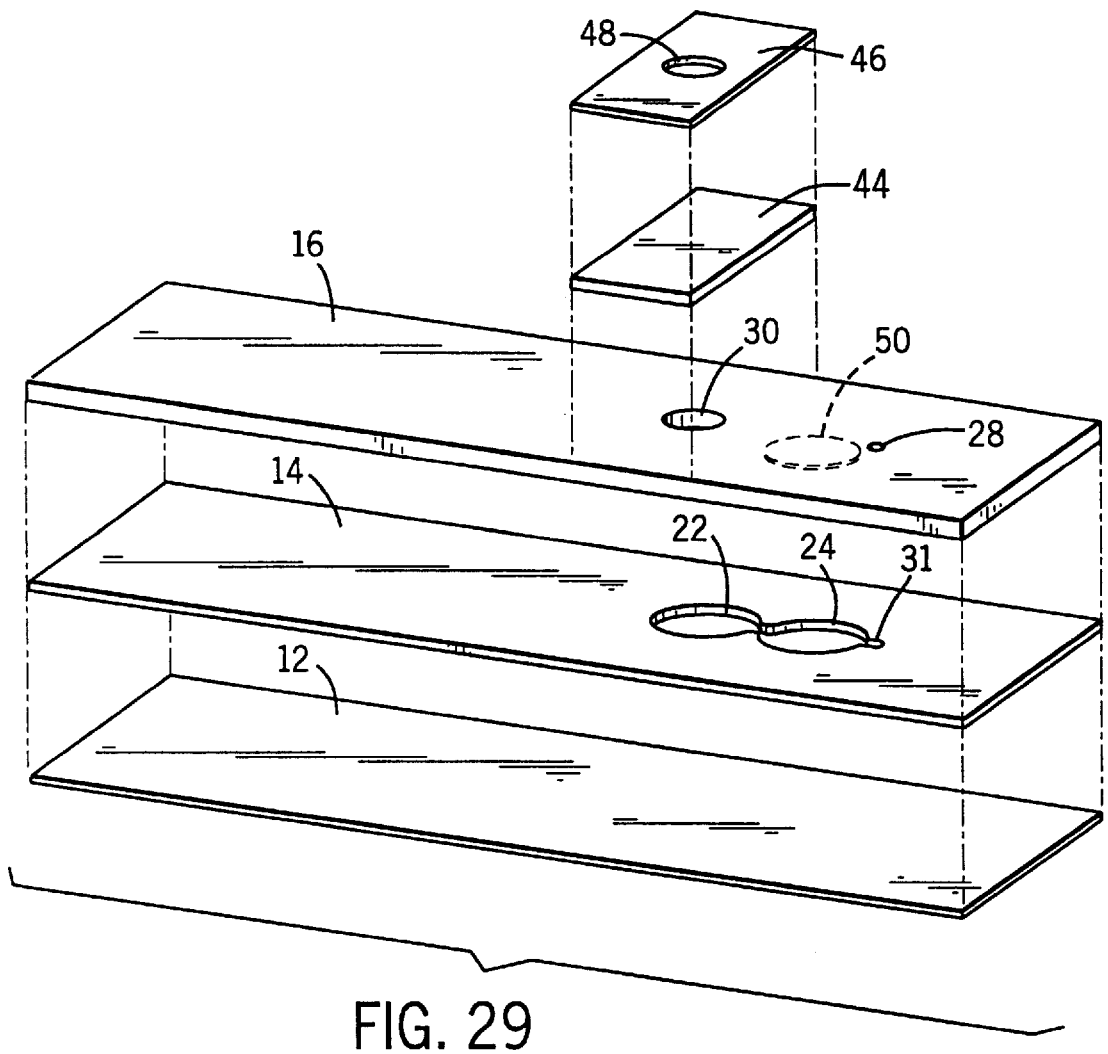
FIG. 29 is an exploded perspective view of a multiple-layer element showing the deposition of a light-absorbing colorant in a fluid-transporting layer, which overlies the sample introduction chamber. In this element, the liquid sample is applied to the fluid-transporting layer, thereby dissolving or dispersing the colorant, and the resulting solution or dispersion is then transported into the optical reading chamber, which contains the dried reagent.
Figure 30:
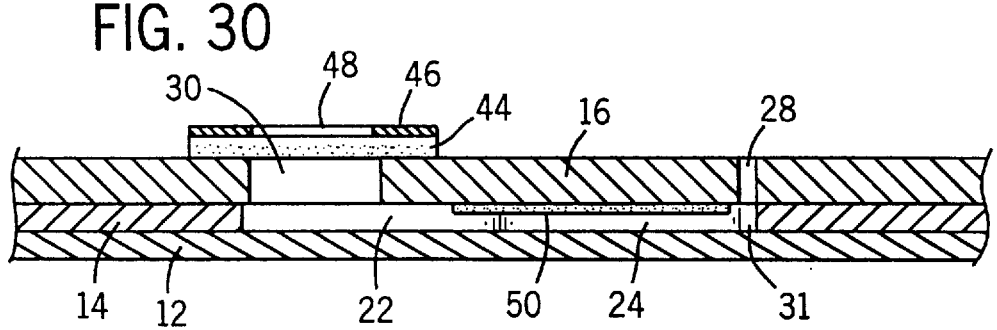
FIG. 30 is a cross-sectional view corresponding to FIG. 29, showing the vent opening, the sample introduction site opening, the sample introduction chamber, and the optical reading chamber.

In an alternative embodiment, the colorant can be deposited in a fluid-transporting layer overlying the sample introduction chamber and in register therewith. FIGS. 29 and 30 illustrate an embodiment of a multiple-layer element in which a colorant is deposited in a fluid-transporting layer overlying the sample introduction chamber and in registration therewith. The fluid-transporting layer is represented by the reference numeral 44. The remaining components of the multiple-layer element in FIGS. 29 and 30, i. e., the base layer 12, the core layer 14, the cover layer 16, the sample introduction chamber 22, the optical reading chamber 24, the vent opening 28, the sample introduction site opening 30, and the vent channel 31, perform the same functions as those components having the same reference numerals in FIGS. 1, 2, 3, and 4. Upon addition of the sample to the fluid-transporting layer, the colorant is dissolved, if a dye, or dispersed, if a pigment. From that point onward, the element operates in the same manner as does the element in the embodiment previously described.

Figure 31:
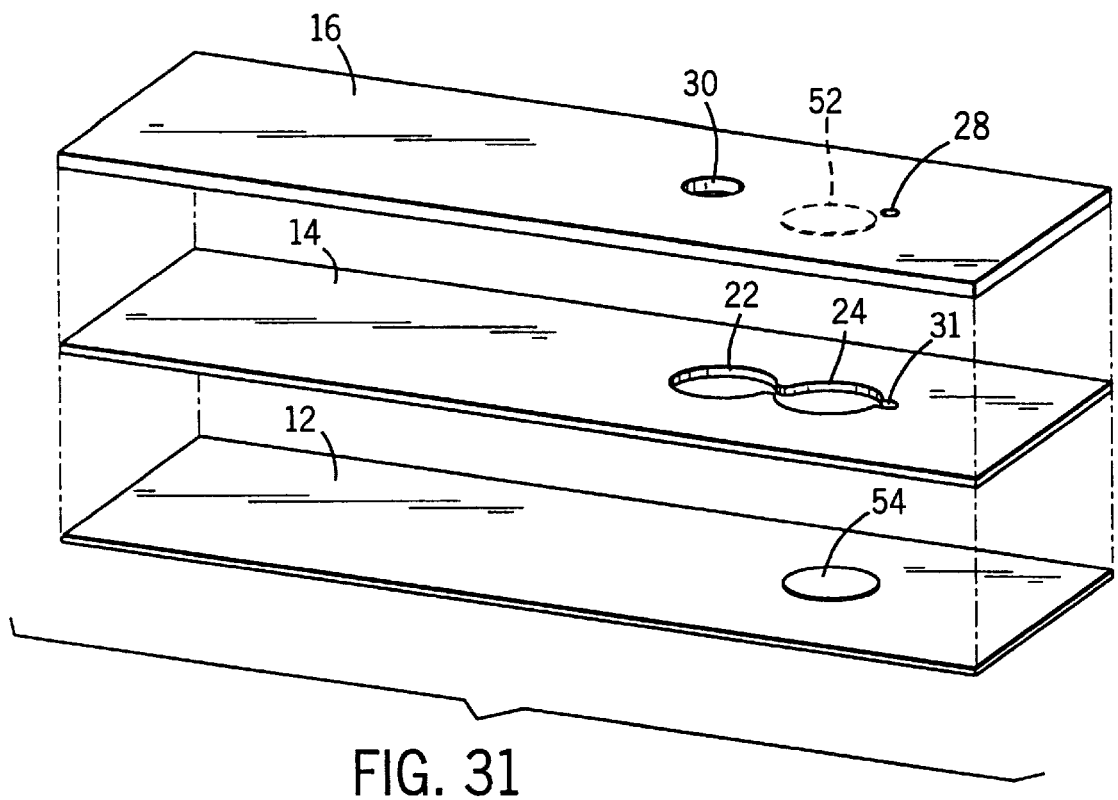
FIG. 31 is an exploded perspective view of a multiple-layer element showing the deposition of a layer of reflective material in the optical reading chamber. Upon entry of a liquid sample into the optical reading chamber, the reflective properties of the layer of reflective material are altered, thereby resulting in a decrease in intensity of light reflected from the layer of reflective material.
Figure 32:
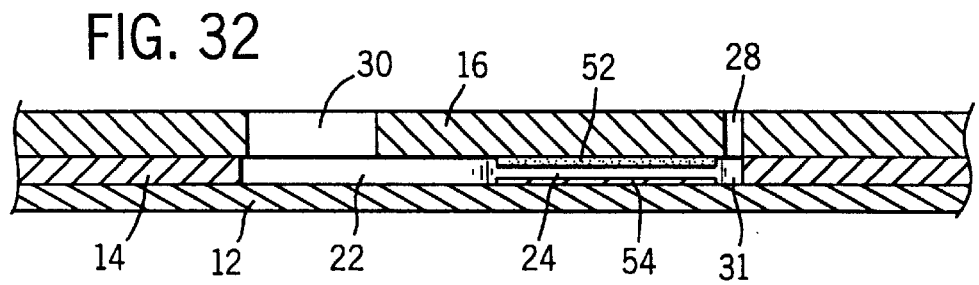
FIG. 32 is a cross-sectional view corresponding to FIG. 31, showing the vent opening, the sample introduction site opening, the sample introduction chamber, and the optical reading chamber.

A layer of a material that changes its reflectance in the presence of a liquid can be used to determine when the optical reading chamber contains a sufficient amount of sample for the determination of the concentration of an analyte. This layer can be applied onto the surface of the cover layer that faces the optical reading chamber. At least a portion of this layer must be in register with the optical path of the optical reading chamber. Two types of such indicating layers have been considered. The first type involves a layer of a material that is highly reflective when dry on account of a large number of interfaces between the air and the material. Because of the difference in index of refraction between the highly reflective material and air, the light used for measurement is easily reflected. This layer of material is applied to the surface of the cover layer that faces the optical reading chamber. When liquid sample reaches the optical reading chamber, the index of refraction difference between the reflective material and the liquid sample is much less, and less light is reflected from the reflective surface, thereby allowing some light to escape through the layer of the highly reflective material, causing a characteristic drop in reflectance. FIGS. 31 and 32 illustrate an embodiment of a multiple-layer element in which a layer of highly reflective material is applied to the surface of the cover layer that faces the optical reading chamber. The highly reflective material is designated by the reference numeral 52. The reference numeral 54 represents a layer of reagents. The remaining components of the multiple-layer element in FIGS. 31 and 32, i. e., the base layer 12, the core layer 14, the cover layer 16, the sample introduction chamber 22, the optical reading chamber 24, the vent opening 28, the sample introduction site opening 30, and the vent channel 31, perform the same functions as those components having the same reference numerals in FIGS. 1, 2, 3, and 4.

Figure 33:
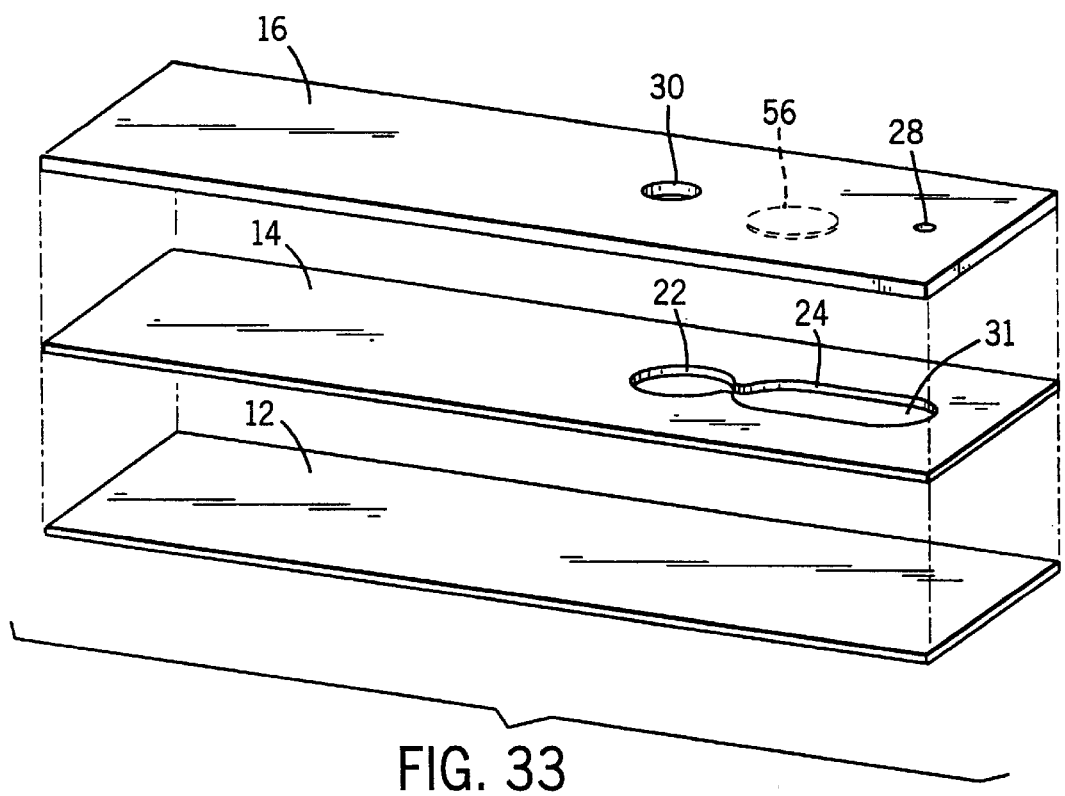
FIG. 33 is an exploded perspective view of a multiple-layer element showing the deposition of a layer of reflective material in the optical reading chamber. Upon entry of a liquid sample into the optical reading chamber, the layer of reflective material is dissolved or dispersed, and then washed out of the optical reading chamber by the sample, thereby resulting in a decrease in the intensity of light reflected from the layer of reflective material as light is absorbed by or transmitted through the top layer of the multiple-layer element.
Figure 34:
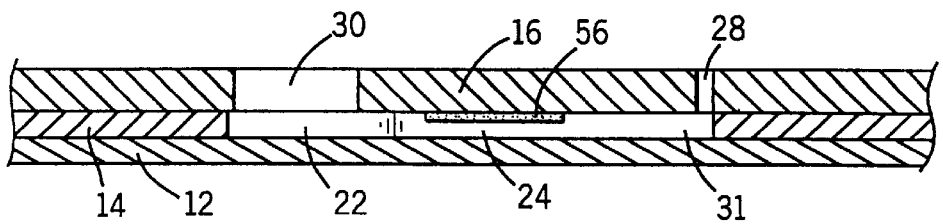
FIG. 34 is a cross-sectional view corresponding to FIG. 33, showing the vent opening, the sample introduction site opening, the sample introduction chamber, and the optical reading chamber.

The second type of indicating layer employs a layer of a highly reflective material coated onto the surface of the cover layer that faces the optical reading chamber. In this embodiment, however, the highly reflective coating is washed out of the optical path of the optical reading chamber by the liquid sample. When the layer of highly reflective material is washed out of the optical path, the remaining material of the surface of the cover layer that faces the optical reading chamber provides a less reflective surface. The reflectivity of the layer of highly reflective material can be controlled to a specific level. Thus, when the liquid sample is introduced, the layer of highly reflective material is washed out of the optical path of the optical reading chamber and the intensity of the light reflected decreases, thereby indicating the addition of a sample. FIGS. 33 and 34 illustrate an embodiment of a multiple-layer element in which a layer of highly reflective material is coated onto the surface of the cover layer that faces the optical reading chamber. The highly reflective material is designated by the reference numeral 56. The remaining components of the multiple-layer element in FIGS. 33 and 34, i. e., the base layer 12, the core layer 14, the cover layer 16, the sample introduction chamber 22, the optical reading chamber 24, the vent opening 28, the sample introduction site opening 30, and the vent channel 31, perform the same functions as those components having the same reference numerals in FIGS. 1, 2, 3, and 4. The optical reading chamber 24 is elongated to permit the reflective material to be washed out of the optical path.

The sample introduction chamber may contain a blood separation filter. The blood separation filter can be any type of material that removes some or all of the red blood cells from the sample. For some applications, no red blood cells are desired. For other applications, some red blood cells are required. For example, some red blood cells may be required for calibrating certain optical instruments. Three major categories of filters suitable for use as a blood separation filter in the sample introduction chamber are red blood cell aggregating matrix, affinity binding support, and cellular exclusion. Red blood cell aggregating matrix comprises a matrix coated with a positively charged polymer. For example, positively charged polymers suitable for use in this application include polylysine, polybrene protamine, etc. See, for example, U.S. Pat. No. 5,658,444, incorporated herein by reference.

The second category involves the immobilization of antibodies to red blood cells (anti-RBC) or lectin on a matrix by means of covalent linking or passive absorption. The immobilized anti-RBC or lectin bind specifically to red blood cells and thereby separate them from serum or plasma. The third category of matrix separates red blood cells on the basis of cellular size and/or the size of pores of the matrix. In this category, the red blood cells are restricted from passing through the matrix because the pores in the matrix have a size that is too small for passage of red blood cells. There are two types of molecular sizing matrices—(1) symmetric pore size and (2) asymmetric pore size. The matrix having symmetric pore size provides a single and homogeneous pore size, whereas in the asymmetric matrix, pore sizes vary from smaller to larger. In the latter case, pores of larger size are at the top of the matrix and the size of the pores gradually decreases toward the base of the matrix.

For some applications in which the instrument can correct for hemoglobin interference, one can use blood lysate instead of plasma or serum for analysis. In this case, the matrix can be coated with lysing agent, such as "TRITON X-100", saponin, or "IGEPAL."

The optical reading chamber contains the reagent(s) required for reacting with the analyte of interest. A typical reagent coating formulation comprises the following ingredients in the amounts indicated:

TABLE II

| Ingredient | Amount |
| --- | --- |
| Glucose dehydrogenase | 5–1000 units/mL |
| Diaphorase | 5–1000 units/mL |
| β-Nicotinamide adenine dinucleotide | 30–200 mM |
| 3-[4,5-Dimethylthiazol-2-yl]-2,5-diphenyltetrazolium bromide | 30–90 mM |
| Tris (hydroxymethyl) aminomethane buffer | 100 mM |

The reagent composition can be applied to the optical reading chamber by means of coating. Various means of coating the reagent composition that are suitable for use in this invention are described in the *Kirk-Othmer Encyclopedia of Chemical Technology*, 4$^{th}$ edition, Vol. 6, John Wiley & Sons, Inc. (New York:1993), pp. 606–669, incorporated herein by reference. Coating thickness of the reagent composition is not critical; however, care must be taken so that the amount of reagent coated is sufficient to determine the concentration of glucose within a reasonable amount of time at the highest possible concentrations of glucose in blood. The ranges set forth in the foregoing table are not critical and they can be varied as desired.

Another aspect of this invention involves a method for determining the concentration of an analyte, e. g., glucose, in a sample of biological fluid, e. g., blood. The method comprises the steps of:

(a) introducing a sample of biological fluid, e. g., blood, from the body of a patient to a multiple-layer element comprising a sample introduction chamber and a optical reading chamber;

(b) allowing a reagent in the multiple-layer element to react with the analyte of interest in the sample; and (c) measuring the concentration of analyte in the sample by optical instrument.

Detection of analyte is carried out by measuring the change in an optical property of the material in the optical reading chamber resulting from one or more reactions involving the analyte with one or more reagents. Preferably, the change in optical property is a change in reflectance, which change can be observed by an optical instrument. In the case of determination of glucose, the reagents typically include at least one enzyme and at least one dye.

In one assay system for determining concentration of glucose, glucose in the sample is oxidized by glucose oxidase to form gluconic acid and $H_2O_2$. The amount of $H_2O_2$ produced is then measured quantitatively by Reaction (1) or Reaction (2).

Reaction (1)

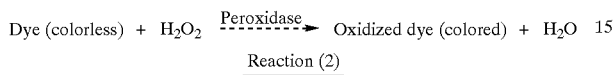

Reaction (2)

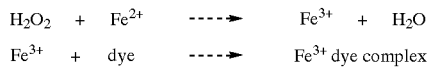

In Reaction (1), the enzyme peroxidase (e. g., horseradish peroxidase, microperoxidase) catalyzes the oxidation of the dye and converts $H_2O_2$ to $H_2O$. The color intensity is directly proportional to the concentration of glucose in the sample. Representative examples of dyes that have been used include o-dianisidine, 4-aminoantipyrine, and 3,5-dichloro-2-hydroxybenzenesulfonate.

In Reaction (2), $H_2O_2$ oxidizes the $Fe^{2+}$ to $Fe^{3+}$. $Fe^{3+}$ then chelates with dye to produce a specific absorption peak. Representative examples of ferrous salt include ferrous sulfate and potassium ferrocyanide. Representative examples of the dye include xylenol orange. The amount of $Fe^{3+}$ dye complex that forms is proportional to the amount of glucose in the sample.

In another assay system for determining concentration of glucose, which is preferred for this invention, glucose dehydrogenase enzyme reacts specifically with glucose in the sample in the presence of co-enzyme β-nicotinamide adenine dinucleotide (β-NAD) to form NADH, the reduced form of β-NAD. The NADH reacts with an electron accepting dye, e. g., 3-[4,5-dimethylthiazol-2-yl]-2,5-diphenyltetrazolium bromide (MTT), catalyzed by the diaphorase enzyme to form a dark purple-reddish color. The color intensity measured at 640 nm is directly proportional to the concentration of glucose in the sample.

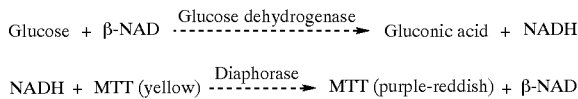

In both systems, detection is carried out by means of optical measurement. The measurement can be of reflection of light. The specimens suitable for the method include, but are not limited to, blood, plasma, serum, interstitial fluid, and blood lysate.

The glucose dehydrogenase system and other systems that are not dependent upon oxygen are preferred for the article and method of the present invention, because these systems are capable of reacting with the analyte in an environment having a limited amount of oxygen. In a system where oxygen is required, the reaction may never be able to indicate concentrations of analyte at the high end of the dynamic range because the amount of oxygen available to the system may be insufficient to allow the reaction to reach completion.

Preparation of Multiple-layer Element

The article of this invention, i. e., the multiple-layer element, can easily be prepared by processes well-known to those of ordinary skill in the arts of die punching and laminating. For embodiments of the type shown in FIGS. 1, 2, 3, and 4, the core layer 14 can be prepared by forming the sample introduction chamber 22, the optical reading chamber 24, and the vent channel 31 by means of die punching or laser cutting. If desired, a flow channel of the type shown in FIGS. 9, 10, 11, and 12 can also be formed by the same techniques. The cover layer 16 can be prepared by forming the vent opening 28 and the sample introduction site opening 30 by means of die punching or laser cutting. The base layer 12 can be laminated to one major surface 20 of the core layer 14 by means of heat sealing or an adhesive. The reagent can then be deposited into the optical reading chamber 24 by means of an appropriate coating technique. Finally, the cover layer 16 can be laminated to the other major surface 18 of the core layer 14 by means of heat sealing or an adhesive. For embodiments of the type shown in FIGS. 5, 6, 7, and 8, the base layer 112 can be prepared by forming the sample introduction chamber 122, the optical reading chamber 124, and the vent channel 131 by means of embossing or laser cutting. If desired, a flow channel of the type shown in FIGS. 9, 10,11, and 12 can also be formed by the same techniques. The cover layer 116 can be prepared by forming the vent opening 128 and the sample introduction site opening 130 by means of die punching or laser cutting. The reagent can then be deposited into the optical reading chamber 124 by means of an appropriate coating technique. Finally, the cover layer 116 can be laminated to the major surface 118 of the base layer 112 by means of heat sealing or an adhesive.

Operation

Biological fluid, such as, for example, blood, can be obtained by means of a conventional fingerstick. Methods and apparatus for obtaining blood are well-known to those of ordinary skill in the art. Examples of apparatus suitable for obtaining a sample of blood are described in U.S. Pat. Nos. Re. 32,922; 4,203,446; 4,990,154; 5,487,748, all of which are incorporated herein by reference. For the sake of better understanding, the remaining steps of the operation of the multiple-layer element will refer to FIGS. 1, 2, 3, and 4. However, the operation would not change if the embodiment employed was that of FIGS. 5, 6, 7, 8, 9, 10, 11, 12, 13, 14, 15, and 16. After the sample of blood is obtained, the required amount of sample is introduced to the multiple-layer element 10 by applying the sample through the sample introduction site opening 30. The sample then flows to the sample introduction chamber 22, from whence it flows to the optical reading chamber 24 and the vent channel 31. The sample can flow from the sample introduction chamber 22 to the optical reading chamber 24 either directly, or through a flow channel, if one is present. A flow channel is shown in FIGS. 9, 10, 11, and 12. The flow of sample terminates when the vent channel 31 is reached. The concentration of analyte can be determined by an optical instrument, e. g., a "LIFES-CAN" glucose meter, which senses the presence of a sample contained in the multiple-layer element and makes the determination of concentration a short time thereafter. In the embodiment shown in FIGS. 1, 2, 3, and 4, the notched end of the multiple-layer element is the end that is first inserted into the "LIFESCAN" glucose meter.

It is critical that the optical reading not be taken until the optical reading chamber contains a sufficient amount of sample. The reason for this requirement is that an insufficient amount of sample will provide an inaccurate result. There are several useful methods for determining if the optical reading chamber contains a sufficient amount of sample. In one preferred method, the liquid sample is brought into contact with a colorant, such as, for example, a soluble dye. The colorant alters the optical properties of the liquid sample prior to the introduction of the sample into the optical reading chamber of the device. After the sample has entered the optical reading chamber, a change in the reflectance or transmission of light in the optical reading chamber is detected, thereby indicating that the sample has entered the optical reading chamber. The level of change in reflectance, or transmission, is then used to indicate whether the optical reading chamber contains a sufficient amount of sample for the determination of the concentration of glucose. If the volume of the sample is insufficient, or if air bubbles have been trapped in the optical reading chamber, the insufficiency of the sample in the optical reading chamber is indicated by the lower level of change in reflectance or transmission.

Colorants that can be used in this invention must not adversely affect the properties of the sample or the assay reagents. The colorant must also not adversely affect the design of the optical reading chamber. The colorant should have minimal interaction, or predictable interactions, with the sample. Aggregation, precipitation, or spectral shifts of the colorant are not preferred; however, predictable changes, such as the use of a pH indicator dye could be used. The selected colorant should be non-interfering with the reagents required for the determination of the concentration of the analyte of interest. Colorants that absorb light at the same wavelength required for the assay can still be used. Light having a wavelength different from that required for the analyte determination but selective for the colorant can be used to provide an appropriate correction to the measurement. Finally, the colorant must be compatible with the materials of the multiple-layer element and must possess properties that allow adequate detection in the element.

Dyes that are suitable as the colorant must readily be dissolved or dispersed by the liquid sample, with a degree of solubility sufficient to allow detection by optical means. Such a degree of solubility is preferably greater than 1 mg/ml of sample, and more preferably greater than 10 mg/ml of sample. Water-soluble dyes are preferred for use with biological fluids.

Pigments, such as colored colloids, can be used as a colorant in this invention, but pigments suitable for the invention must rapidly and uniformly disperse throughout the liquid sample. The use of pigments has not been as reliable as the use of soluble dyes on account of interactions of the pigments with the samples.

The colorant must exhibit sufficient absorbance to be detected (preferably greater than 1000 mol $^{-1}$cm$^{-1}$, and more preferably greater than 10,000 mol $^{-1}$cm$^{-1}$ at the wavelength of detection). Representative examples of dyes that are suitable for use in this invention include, but are not limited to, Acid Black 2, Acid Black 48, Acid Green 41, Indocyanine Green, Copper Phthalocyaninetetrasulfonic acid, Eriochrome Black T, Gallocyanine, and Janus Green B. Representative examples of pigments that are suitable for use in this invention include, but are not limited to, colloidal carbon and polypyrrole.

In another preferred method, two techniques, both of which use layers of reflective material, can be used in order to bring about a change in reflectance in the optical path of the optical reading chamber, thereby indicating addition of sample. In the first technique, a layer of material that is highly reflective when dry is applied to the surface of the cover layer that faces the optical reading chamber. Representative examples of such materials include, but are not limited to, controlled pore glass, controlled pore silica, latex microparticles, and porous hydrophilic membranes. These materials are highly reflective on account of the large number of interfaces between air and the highly reflective material making up the layer. Because of the difference in index of refraction between the material of the layer and air, the light used for measurement is easily reflected. When the liquid sample is added, the difference in index of refraction mismatch between the reflective material and the liquid sample is much less, and less light is reflected, thereby allowing some light to escape through the layer to bring about a characteristic change in reflectance.

The second technique employs a highly reflective material coated on the surface of the cover layer that faces the optical reading chamber. Representative materials suitable for this highly reflective coating are titanium oxide, zinc oxide, and barium sulfate. In this technique, however, the coating of highly reflective material is washed out of the optical path of the optical reading chamber by the liquid sample. When the coating of highly reflective material is washed out of the optical path, the material of the surface of the cover layer that faces the optical reading chamber provides a less reflective surface. The reflectivity of the coating of highly reflective material can be controlled to a specific level. Thus, when the sample is introduced, the coating is washed out of the optical path and a change in reflectance is generated, thereby indicating addition of the sample.

Changes in reflectance resulting from red blood cells, or hemoglobin, have been used in the past. The red cell component of blood can be used to detect the presence of a liquid sample in the optical reading chamber. However, in some designs of the multiple-layer element of this invention, the short optical path of the optical reading chamber prevents the sample by itself from bringing about detectable optical changes in the optical reading chamber. This design problem has the disadvantage of making it difficult to determine if the optical reading chamber contains a sufficient amount of sample for carrying out the assay. The use of the red cell component of the blood would also preclude the use of other biological fluids that lack the hemoglobin chromophore. Dependence on the chromogenic properties of the sample also has the disadvantage of unpredictable or variable changes in optical properties of the sample, which could affect the results, or limit the type of sample that could be used in the element.

The methods of this invention also have the potential to be used in detection instruments based on transmission of light. By using transmissive materials for the exterior faces of the optical reading chamber, any of the methods result in a measurable change in light transmission upon entry of sample into the optical reading area.

The article of this invention allows for extremely accurate control of volume of sample. Even if the volume of the sample exceeds the volume required for the determination of the concentration of analyte, the article is unaffected by the excess volume of sample. Red blood cells can be present in the optical reading chamber without adversely affecting the accuracy of the reading. Blood lysate can be used in the article and method of the invention. The use of lysate reduces optical interference by providing a homogeneous sample for testing. The employment of a vent allows the article to prevent air lock, which would result in air bubbles and yield false readings. Blood samples having a high hematocrit do not affect the time required to provide a result. The article is designed so that blood cannot leak through it, thereby reducing the likelihood of contaminating the meter. The article is designed so that evaporation of sample is minimized and the effects of humidity are minimized.

The article and method of this invention can be adapted for measuring the concentration of analytes other than glucose. Such analytes include, for example, cholesterol, uric acid, BUN (blood urea nitrogen), and creatinine.

The article and method of this invention can be adapted to employ other optical measurement systems, such as for example, systems employing fluorescence, chemiluminescence, or fluorescence polarization.

The following non-limiting examples are intended to further illustrate the invention.

EXAMPLES

Example 1

This example demonstrates that a reagent comprising hexokinase, glucose-6-phosphate dehydrogenase, and diaphorase can be used in an assay employing the "LIFESCAN" "ONE TOUCH" glucose meter.

A reagent mixture containing the following ingredients in the concentrations indicated was used:

| | |
|---|---|
| Tris (hydroxymethyl) aminomethane buffer (hereinafter "Tris buffer") | 200 mM, pH 7.0 |
| MgCl$_2$6H$_2$O | 100 mM |
| Adenosine 5'-triphosphate (hereinafter "ATP") | 50 mM |
| β-Nicotinamide adenine dinucleotide (hereinafter "β-NAD") | 48 mM |
| 3-[4,5-dimethylthiazol-2-yl]-2,5-diphenyl-tetrazolium bromide (hereinafter "MTT") | 20 mM |
| Hexokinase | 125 Units/mL |
| Glucose-6-phosphate dehydrogenase (hereinafter "G-6-PDH") | 125 Units/mL |
| Diaphorase | 125 Units/mL |

Figure 17:
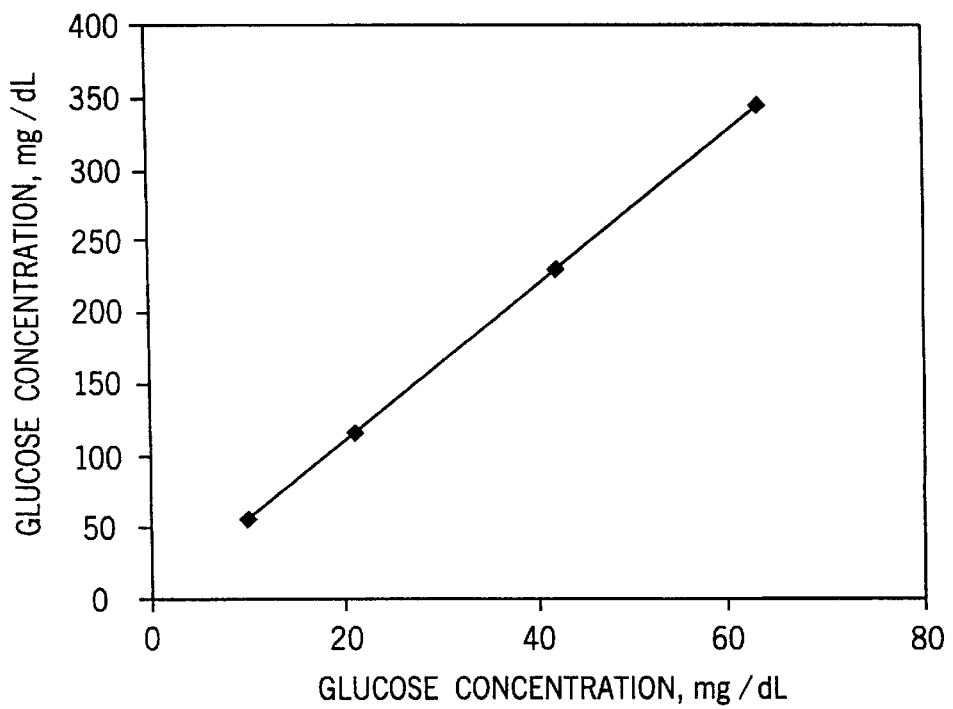
FIG. 17 is a graph comparing the multiple-layer element of this invention with a "ONE TOUCH" test strip in a "ONE TOUCH" glucose meter.
Figure 26:
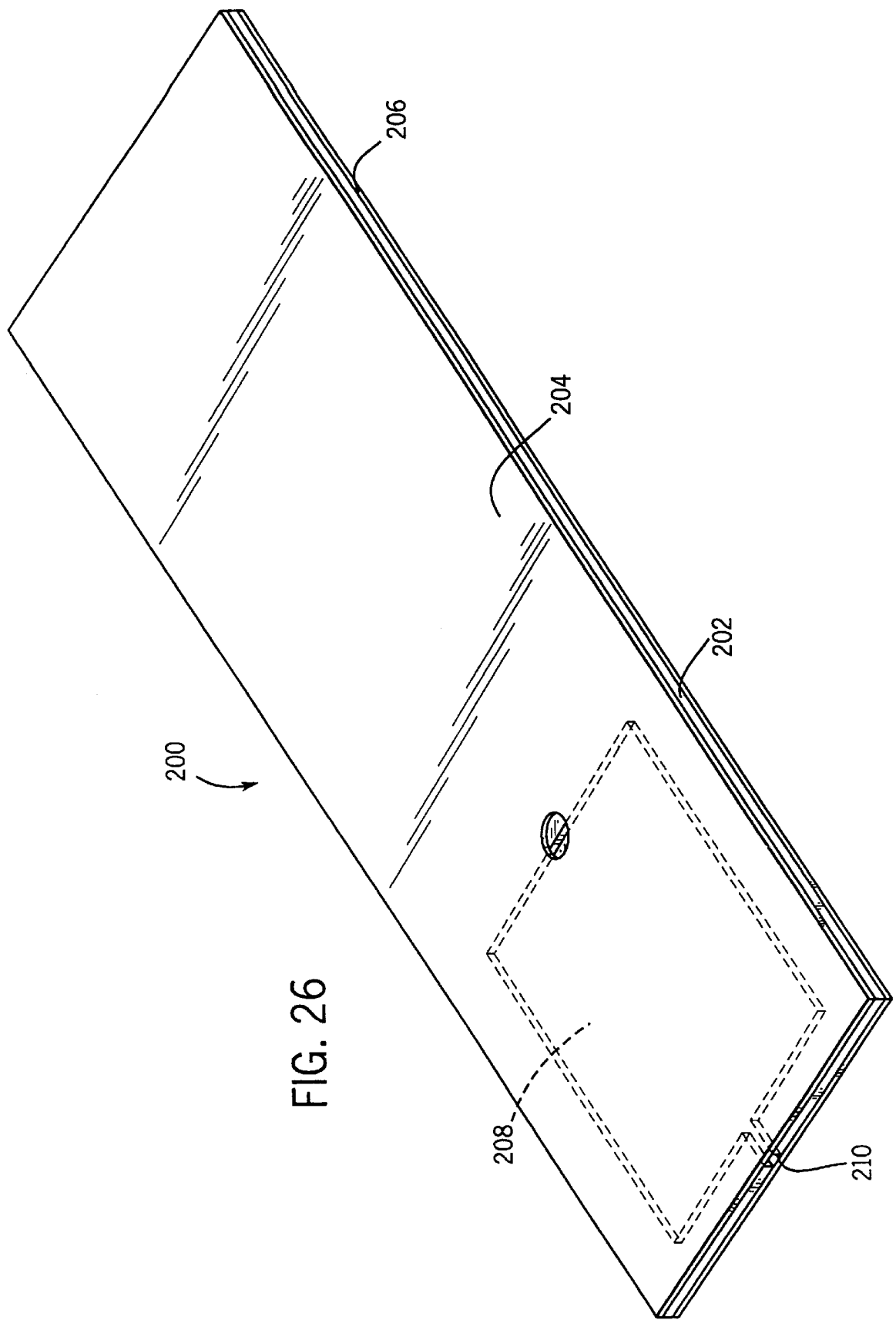
FIG. 26 is a perspective view of a test strip that was used in Example 1.

For each concentration of glucose solution, the reagent (10 μL) was mixed with the glucose solution (100 μL) and the resulting mixture introduced into a multiple-layer element 200 as shown in FIG. 26 by capillary attraction. The multiple-layer element 200 comprised a core layer 202, a cover layer 204, and a base layer 206. The mixture was introduced to an optical reading chamber 208 via a flow channel 210. The major surface of the cover layer 204 in register with the optical reading chamber 208 was coated with a white material ("LIQUID PAPER" correction fluid), which provided good reflectivity of incident light from the optical instrument of the "ONE TOUCH" glucose meter. The decrease of reflectance resulting from light absorption by the colored product formed from the reaction was monitored by the "ONE TOUCH" glucose meter. The reading was taken 45 seconds after the mixture was introduced into the multiple-layer element. Glucose solutions of 10.5, 21, 41.5, and 62.5 mg/dL were reacted with the reagent. In FIG. 17, the reading obtained with the element of FIG. 26 at a given concentration of glucose and the reagent of this example (ordinate) was recorded as a unction of the reading obtained with a "ONE TOUCH" test strip at that given concentration (abscissa).

The reagent of this example was 5.4 times more sensitive than the reagent employed in the "ONE TOUCH" test strip, i. e., glucose oxidase. In other words, for a given glucose concentration, the reading obtained with the reagent of this invention was about 5.4 times the reading obtained with a "ONE TOUCH" test strip. The results demonstrate that the reagent of this example was compatible with the "ONE TOUCH" glucose meter. The wavelength of light for the glucose determination ranged from 590 to 640 nm. The wavelength of light utilized in the "ONE TOUCH" glucose meter was 635 nm. The reagents used in the "ONE TOUCH" test strip utilized a glucose oxidase system, which is adversely affected by interferents, such as bilirubin and ascorbic acid. It is believed that that the hexokinase/glucose-6-phosphate dehydrogenase system of this example is subject to lower interference from blood components than is the glucose oxidase system.

Example 2

This example demonstrates the reaction rates of two different reagents suitable for use in a glucose assay employing the multiple-layer element of this invention. The first reagent system included hexokinase, G-6-PDH, and diaphorase. The second reagent system includes glucose dehydrogenase and diaphorase. The hexokinase-containing system was same system that was used in Example 1. The glucose dehydrogenase-containing system contained the following ingredients in the concentrations indicated:

| | |
|---|---|
| Glucose dehydrogenase | 400 units/mL |
| Diaphorase | 200 units/mL |
| β-NAD | 90 mM |
| MTT | 24 mM |
| Tris buffer | 100 mM, pH 7.0 |

Figure 18:
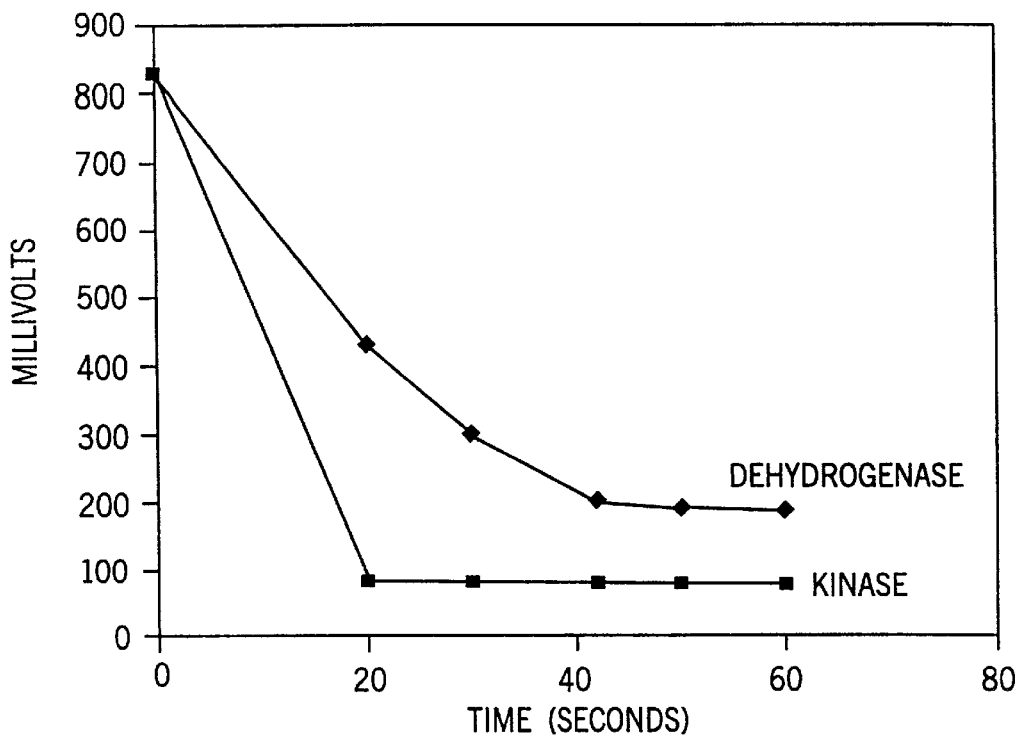
FIG. 18 is graph comparing the reaction rate of a system utilizing hexokinase with a system utilizing glucose dehydrogenase.

For each concentration of glucose solution, the reagent (3 μL) was mixed with the glucose solution (3 μL) and immediately introduced to the multiple-layer element via the sample introduction site opening and the sample introduction chamber. The reaction was then monitored by a reflectance reader, which had been constructed in the laboratory. The reflectance reader utilized a light emitting diode having a peak at 650 nm. Values of the voltage outputs were plotted against time, as shown in FIG. 18. Voltage outputs were a function of reflectance. From the data in FIG. 18, it can be seen that the hexokinase-containing system exhibited better reaction kinetics than did the glucose dehydrogenase-containing system.

Example 3

This example demonstrates another preferred embodiment of the multiple-layer element of this invention. The cover layer comprised gray polymeric film having a semi-reflective coating laminated to a white "BIODYNE" membrane. The "BIODYNE" membrane was a porous hydrophilic membrane (pore size of 1.2 μm) that becomes wetted rapidly and becomes translucent. The cover layer was laminated to one major surface of a core layer, which included the sample introduction chamber and the optical reading chamber. The "BIODYNE" membrane was in face-to-face contact with the core layer. A base layer was then laminated to the opposite major surface of the core layer. The base layer had been coated with a surfactant to improve capillary flow of the sample from the sample introduction chamber to the sample reading chamber. FIGS. 1, 2, 3, and 4 illustrate the construction of the element of this embodiment.

Example 4

This example demonstrates another preferred embodiment of the multiple-layer element of this invention. The element was substantially similar to that of Example 3, with the exceptions that the cover layer was constructed with a white "BIODYNE" membrane having a pore size of 0.45 μm in diameter and no gray polymeric film having a semi-reflective coating was used in conjunction with the "BIO-DYNE" membrane. A transparent top layer was also placed over the white "BIODYNE" membrane. FIGS. 1, 2, 3, and 4 illustrate the construction of the element of this embodiment.

Example 5

This example demonstrates the feasibility of an assay for glucose utilizing reagent formulated with hexokinase and glucose-6-phosphate dehydrogenase as described in Example 1. FIG. 1 is an exploded view of the type of multiple-layer element used in this example. Two substantially cylindrical chambers were formed in the core layer. Each chamber had a diameter of 4.75 mm. The distance between the centers of the two chambers was slightly less than 4.75 mm. The base layer, an acrylic sheet (0.15 mm thick) matted on both sides, was laminated onto one major surface of the core layer. The cover layer, a white polyvinyl chloride sheet having a sample introduction site opening and vent opening, was then laminated onto the opposite major surface of the core layer.

Figure 19:
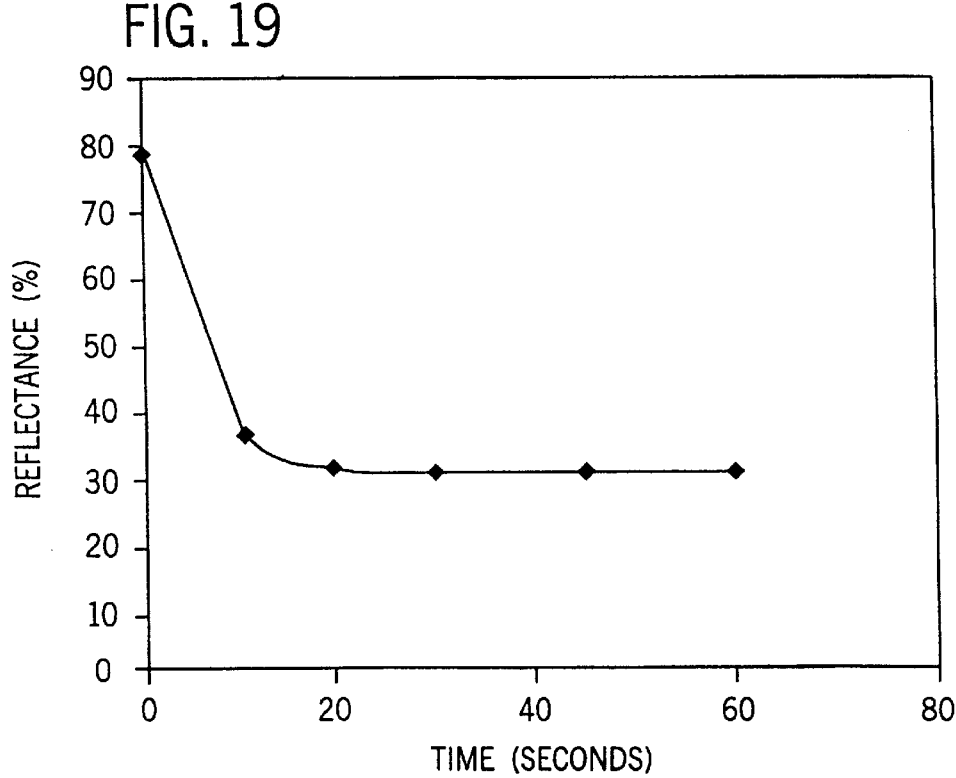
FIG. 19 is graph illustrating the change in reflectance as a function of time.

Glucose solution containing 147 mg/dL of glucose (8 μL) was mixed with reagent (2 μL). The mixture was immediately applied into the multiple-layer element via the sample introduction site opening. The decrease of reflectance at 650 nm caused by light absorption of the colored product formed from the reaction was monitored by means of a reflectance meter. FIG. 19 shows the rapid reaction kinetics provided by the multiple-layer element.

Example 6

Figure 20:
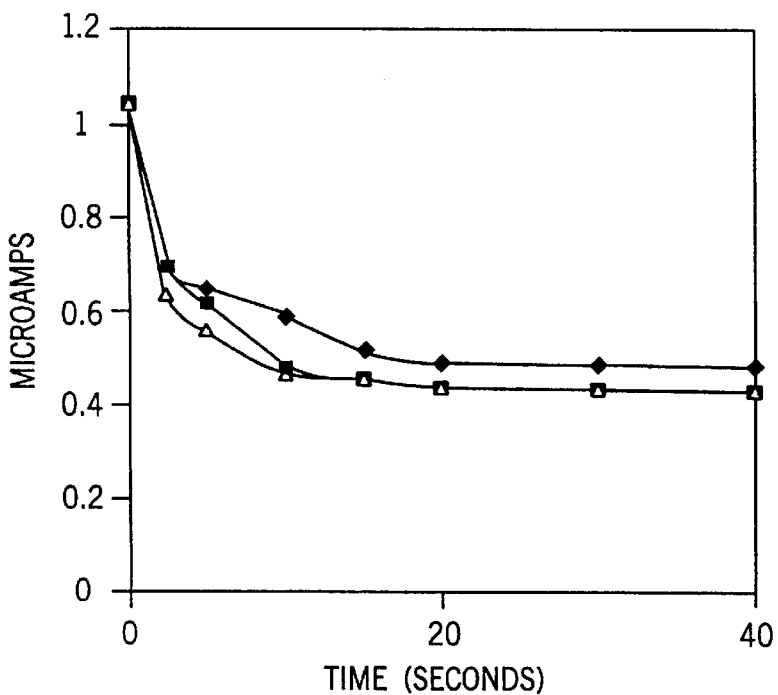
FIG. 20 is graph illustrating the rapid dissolution of the indicator dye.

This example demonstrates the speed at which dried dye dissolves in the optical reading chamber of the multiple-layer element when it comes into contact with a liquid. A base layer was laminated onto one major surface of a core layer as in Example 5. MTT solution (2 μL, 24.0 mM) was transferred by pipette onto the base layer underlying the optical reading chamber and allowed to dry at room temperature. The cover layer, a sheet of polyvinyl chloride, comprising a sample introduction site opening and a vent opening, was laminated onto the other major surface of the core layer. Reagent (8 μL) containing 80 mM NADH, diaphorase (100 Units/mL), 50% serum in 20 mM Tris buffer (pH 7.0) was introduced to the sample introduction site opening. The rate of dissolution of MTT was monitored by measuring the decrease of reflectance as a function of time in the reflectometer. The reflectance was recorded as the current output. FIG. 20 shows the rapid dissolution of MTT in the multiple-layer element. FIG. 20 illustrates three separate runs.

Example 7

This example demonstrates a glucose dose response curve generated with a glucose dehydrogenase/diaphorase system in a multiple-layer element of the type used in Example 3, with the exception that the cover layer of the element was made of polyvinyl chloride. The reagent mixture contained the following ingredients in the mounts indicated:

| | |
|---|---|
| Glucose dehydrogenase (800 units/mL) in Tris buffer (10 mM, pH 7.5) | 10 μL |
| Diaphorase (400 units/mL) in Tris buffer (10 mM, pH 7.5) | 10 μL |
| β-NAD (500 mM) in Tris buffer (10 mM, pH 7.5) | 10 μL |
| MTT (24 mM) in Tris buffer (10 mM, pH 7.5) | 65 μL |

Figure 21:
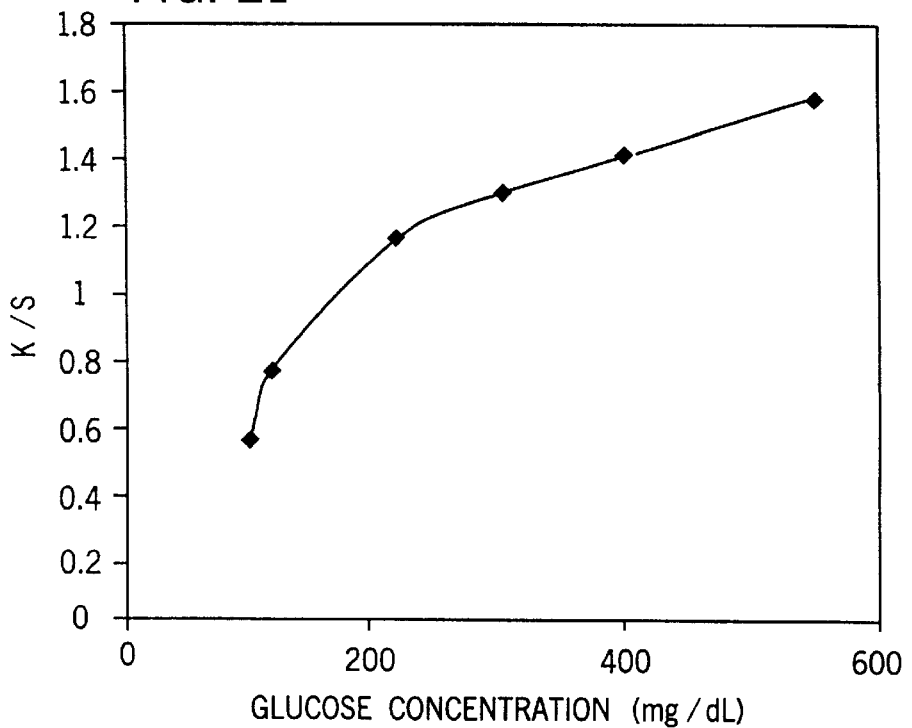
FIG. 21 is a graph illustrating dose response curve of glucose.

To six different aliquots of the foregoing mixture (95 μL) was added glucose solution (5 μL) to make final glucose concentrations of 90, 120, 230, 300, 400, and 550 mg/dL. Each mixture was agitated and immediately applied to a different multiple-layer element. Each reaction was monitored with the "LIFESCAN" "ONE TOUCH" optical system externally driven by a computer. The change of reflectance readings resulting from the colored product formed from the reaction was used in the Kubelka-Munk equation to calculate the concentration of glucose. FIG. 21 shows the glucose dose response curve obtained in this example. The example demonstrated the glucose dose response obtainable with the multiple-layer element of the present invention. The glucose dose response covered the clinically required range of 0 to 550 mg/dL.

Example 8

Figure 22:
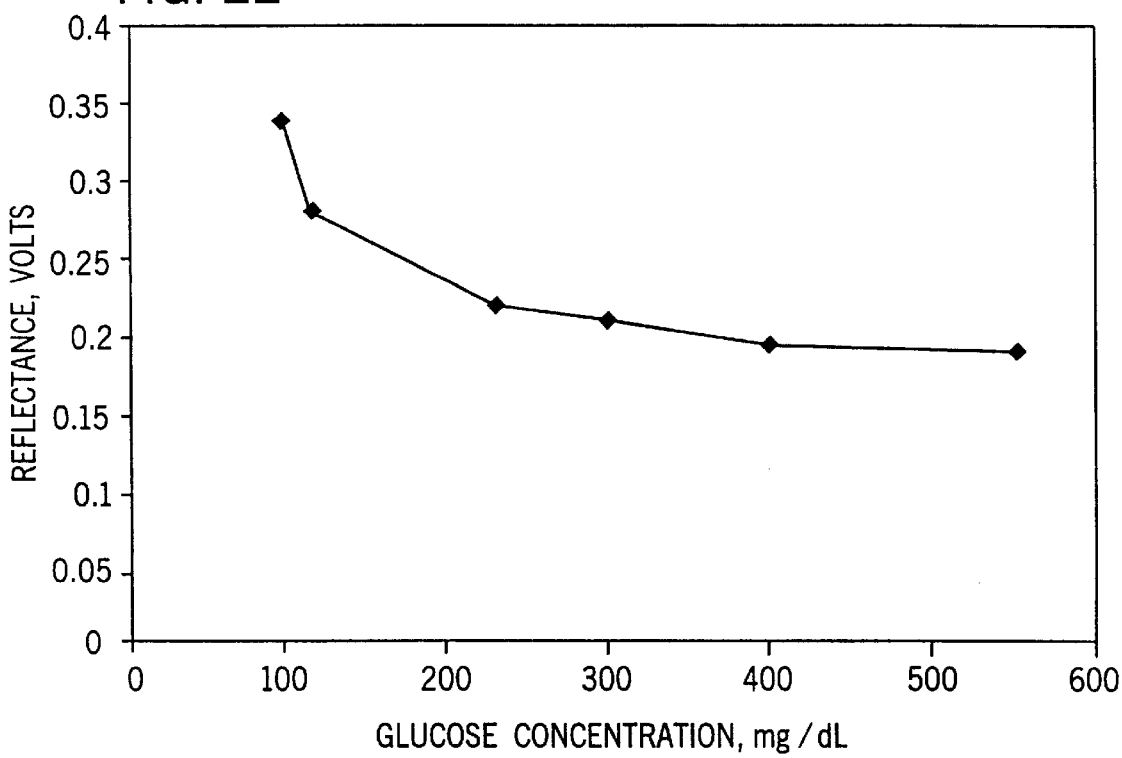
FIG. 22 is a graph illustrating change in reflectance as a function of glucose concentration.

This example demonstrates the feasibility of the reagent used in Example 7 in a multiple-layer element of the type used in Example 7. The reaction of the reagent with glucose was monitored by the change in reflectance readings using the detection system of Example 7. FIG. 22 shows the response of the reflectance reading as a function of glucose concentration. This example demonstrates the feasibility of the multiple-layer element and reagent of this invention with the "LIFESCAN" "ONE TOUCH" glucose meter. In this example, the Kubelka-Munk equation was not used.

Example 9

This example demonstrates the feasibility of using either whole blood or blood lysate as a sample for use in the multiple-layer element of the present invention in the "ONE TOUCH" glucose meter. The element in this example was of the type used in Example 3 and the reagent was of the type used in Example 7.

Fresh venous human blood was obtained and made to contain different levels of hematocrit by centrifugation. The hematocrits obtained were 25, 30, 38, 48, 57, and 63. To whole blood (120 μL) was added reagent (30 μL). The reaction was allowed to proceed for five minutes at room temperature to reach the end point. The reaction mixture was then introduced into the multiple-layer element, and the amount of glucose reacted was then read in the "ONE TOUCH" glucose meter. With the lysate experiment, the whole blood was lysed with 1% "TRITON X-100" lysing agent and the blood lysates were assayed for glucose in the same manner as was employed in the whole blood assay. Two runs were carried out with whole blood and two runs were carried out with blood lysate.

Figure 23:
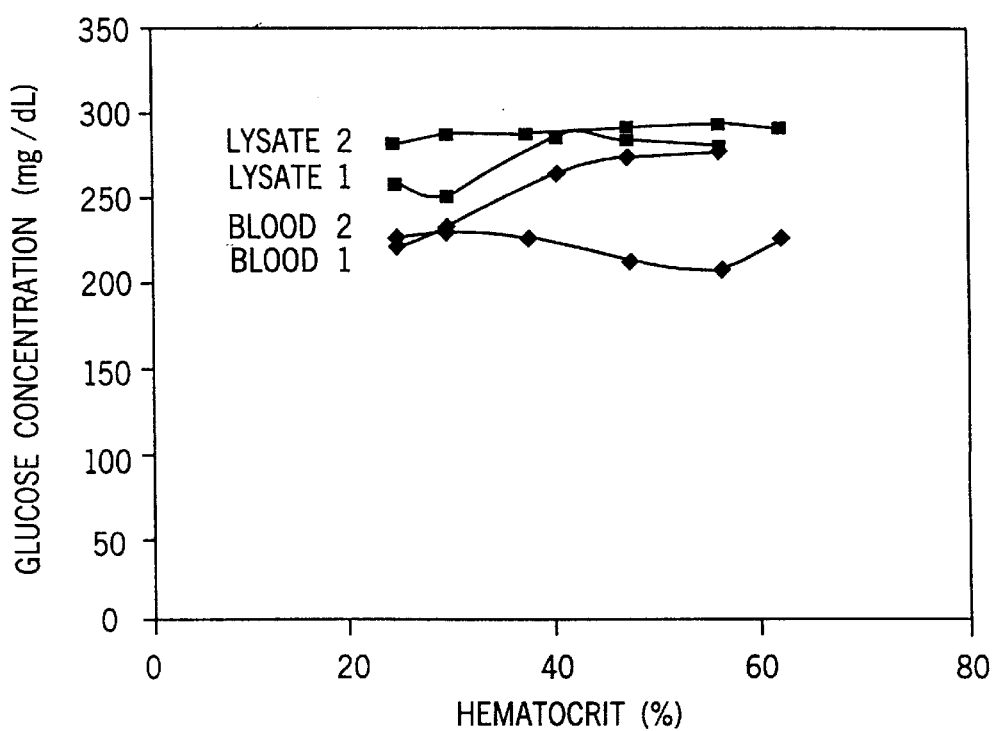
FIG. 23 is a graph illustrating the effect of hematocrit on glucose concentration value.

FIG. 23 shows the results of this example. It can be seen that the effect of hematocrit on glucose value as assayed in the multiple-layer element and the "ONE TOUCH" glucose meter is clinically insignificant. The result suggested that glucose can be measured by the "ONE TOUCH" glucose meter using the multiple-layer element of the present invention, either with a sample of whole blood or with a sample of blood lysate.

Example 10

Figure 24:
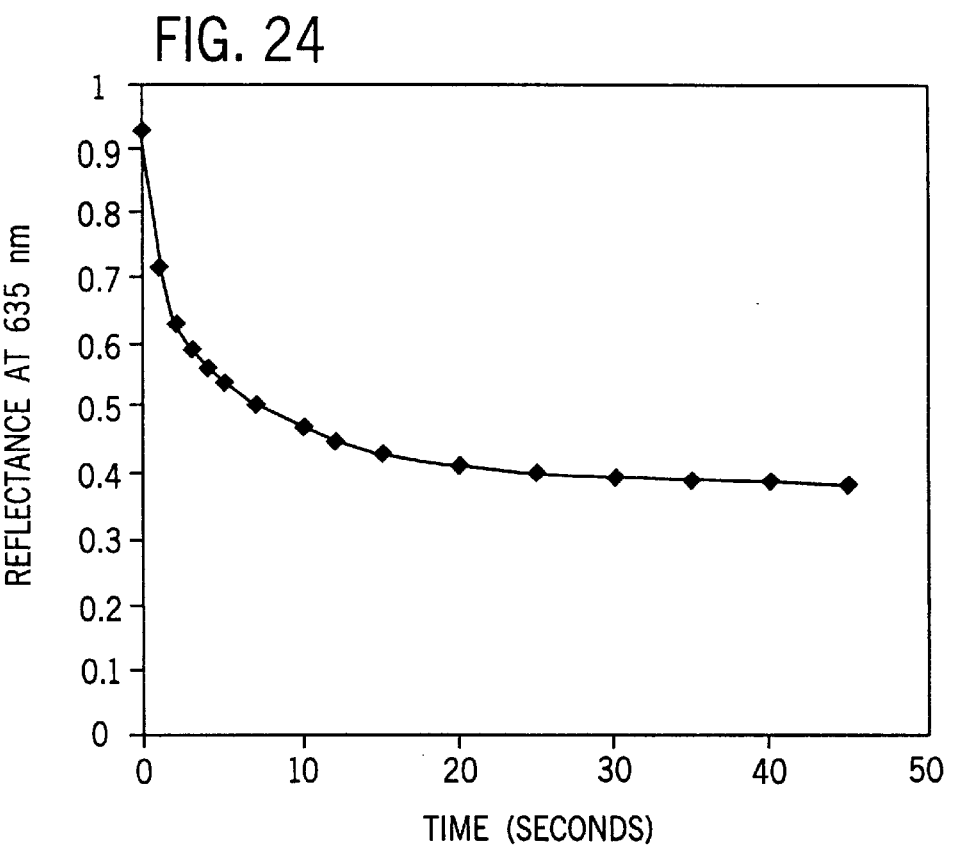
FIG. 24 is a graph illustrating the performance of dried reagent in the multiple-layer element.

This example demonstrates the feasibility of using the multiple-layer element of this invention for glucose measurement in the "ONE TOUCH" glucose meter with the dried reagent in the multiple-layer element. The reagent used was the reagent described in Example 7 and the multiple-layer element used was of the type described in Example 6. Reagent (3 µL) was transferred to the optical reading chamber and dried at room temperature. The cover layer was then applied over the core layer. A drop of blood was then applied to the sample introduction site opening and the reaction was monitored in the detection system described in Example 7. FIG. 24 shows the results of this example. The decrease of reflectance is an indication of the extent of glucose reaction in the element. The reaction proceeded rapidly and the end point was reached in about 20 seconds. It was concluded that the multiple-layer element and reagent are compatible with the "ONE TOUCH" glucose meter.

Example 11

This example demonstrates another preferred embodiment of the multiple-layer element of this invention. The multiple-layer element was similar to the element described in Example 4. The membrane that was used in place of the "BIODYNE" membrane was nitrocellulose (Millipore Corporation), which has a pore size of 0.22 µm. The reagent used in this example employed glucose dehydrogenase. The color-generating dye used in this example was p-iodonitrotetrazolium violet (INT). The glucose dehydrogenase-containing system was prepared by combining the following ingredients in the concentrations indicated:

| | |
|---|---|
| Glucose dehydrogenase | 200 units/mL |
| Diaphorase | 200 units/mL |
| β-NAD | 60 mM |
| INT | 10 mM |
| [4-(2-Hydroxylethyl-1-piperazine propanesulfonic acid] (HEPES) | 100 mM, pH 7.0 |

Figure 25:
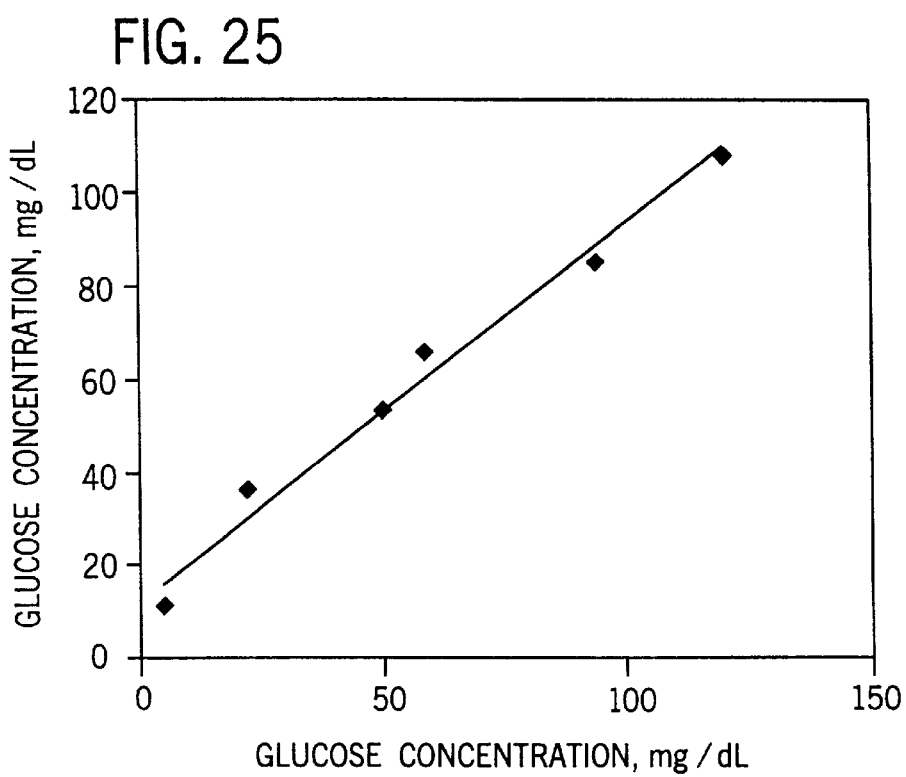
FIG. 25 is a graph comparing the multiple-layer element of this invention with a "ONE TOUCH" test strip in a "ONE TOUCH" glucose meter.

Reagent (one part) was mixed with blood (one part) and the reaction was allowed to proceed for three minutes at room temperature. The reacted mixture (10 µL) was delivered into the optical reading chamber of the device by means of capillary flow from the sample introduction site opening and the sample introduction chamber. The concentration of glucose in the blood was determined in the "LIFESCAN" "ONE TOUCH" glucose meter. In FIG. 25, the reading obtained with the multiple-layer element and the reagent of this example (ordinate) at a given concentration was recorded as a function of the reading obtained with a "ONE TOUCH" test strip at that given concentration (abscissa). It can be seen that the results correlated well with those obtained with a "LIFESCAN" test strip. The slope was 0.99, the intercept was 2.95, and the correlation coefficient was 0.96.

Example 12

This example demonstrates the change in reflectance of a coating in the optical reading chamber of a multiple-layer element upon entry of a liquid sample. The multiple-layer element comprised a white, reflective top layer, having a thickness of 0.250 mm, with openings for the sample introduction site and venting of the optical reading chamber. The bottom layer was a clear acrylic sheet, having a thickness of 0.150 mm, and treated with a surfactant to enhance flow of fluids. The spacer layer, disposed between the top layer and bottom layer, was a polyethylene terephthalate plastic sheet, having a thickness of 0.050 mm, coated on the top and bottom surfaces with adhesive, having a thickness of 0.0125 mm, and with a cut out pattern that defines the optical reading chamber. The reflectance of the empty optical reading chamber at 700 nm was normalized to a value of 1.000. Liquid samples were added to the multiple-layer element, and the relative reflectance (R) of the optical reading chamber was recorded in the absence and presence of Nigrosine (Acid Black 2) at 0.5 mg/ml. The results are shown in Table III.

TABLE III

| Sample | R without dye (700 nm) | R with Nigrosine dye (700 nm) |
|---|---|---|
| Empty cell | 1.000 | N/A |
| Water | 0.875 | 0.530 |
| Urine | 0.875 | 0.528 |
| Whole blood (45% HCt) | 0.786 | 0.519 |

Example 13

This example demonstrates the use of a soluble dye as a colorant added to the sample. The multiple-layer element, which contained the reagents for a determination of concentration of glucose, was prepared as described in Example 10. Buffered solutions of glucose were prepared. Each solution contained 1.0 mg Acid Black 2 per ml. The glucose concentrations of the samples were measured by means of the multiple-layer element with a "ONE-TOUCH" glucose meter. The glucose concentrations measured were then compared to the glucose concentrations of the samples as shown in Table IV.

TABLE IV

| Sample | Actual glucose concentration | Measured glucose concentration | Difference between measured concentration and actual concentration |
|---|---|---|---|
| Blank (water + dye) | 0 | 16 | 16 |
| Low control | 40 | 42 | 2 |
| Normal control | 70 | 79 | 9 |
| Normal control | 70 | 86 | 16 |
| High control | 220 | 234 | 14 |

Example 14

This example demonstrates the preparation of a multiple-layer element according to this invention. The cover layer comprised a clear polyester sheet laminated to a nitrocellulose membrane that becomes more translucent upon wetting. The clear polymeric sheet had a thickness of 0.025 mm and was coated on one major surface with an adhesive having a thickness of 0.013 mm. The nitrocellulose membrane had a pore size of 5 µm and a thickness of 0.125 mm. The cover layer had openings for introduction of sample and for venting of the capillary space. The spacer layer was a polyester sheet having a thickness of 0.050 mm, and was coated on both major surfaces with an adhesive layer having a thickness of 0.013 mm, and a pattern cut out to define a capillary space. The base layer was a clear acrylic sheet having a thickness of 0.150 mm and was treated with a surfactant ("Pluronic L-64") to enhance capillary flow.

Example 15

This example demonstrates how the translucence of the multiple-layer element described in Example 14 increases when a sample enters the optical reading chamber. The reflectance values at 635 nm and at 700 nm of the empty optical reading chamber were set to a value of 1.00. The relative reflectance (R) was recorded following the addition of the sample to the multiple-layer element. The results are shown in Table V.

TABLE V

| Sample | R at 635 nm | R at 700 nm |
| --- | --- | --- |
| None | 1.00 | 1.00 |
| Deionized water | 0.521 | 0.504 |
| Whole blood | 0.380 | 0.405 |

Example 16

This example demonstrates how the translucence of a highly reflective layer increases when a sample enters the optical reading chamber. A mixture containing controlled pore glass in water (1.5 g glass in 8.5 g water) was prepared. The controlled pore glass had the designation of Product No. CPG034000F, Lot No. 11F052, CPG Inc., Lincoln Park, N.J. The mixture (5 μl) was applied to a surfactant-coated acrylic film in a zone 0.187 inch in diameter. The application zone was formed by a pattern cut out of a polymeric film, which was attached to the acrylic film. After the applied mixture had dried, the spots were rehydrated by means of 10 μl of deionized water. The normalized reflectance values at 635 nm and 700 nm were found to be 36.4% and 31.9%, respectively.

The invention described herein has the advantage in that the dominant factor in determining the concentration of an analyte in a sample is that the sample be in the form of a liquid. This advantage results in a greater flexibility in sample properties.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An article suitable for use in determining the concentration of an analyte in a biological sample comprising:
    a multiple-layer element comprising
        (a) a cover layer, said cover layer having a first opening for venting the multiple-layer element and a second opening for receiving a sample of biological fluid; and
        (b) a base layer having a major surface in contact with said cover layer, said base layer or said cover layer or said base layer and said cover layer comprising a sample introduction chamber and an optical reading chamber, wherein said optical reading chamber contains a reagent capable of reacting with glucose, wherein said reagent comprises β-nicotinamide adenine dinucleotide.

2. An article suitable for use in determining the concentration of an analyte in a biological sample comprising:
    a multiple-layer element comprising
        (a) a cover layer, said cover layer having a first opening for venting the multiple-layer element and a second opening for receiving a sample of biological fluid; and
        (b) a base layer having a major surface in contact with said cover layer, said base layer or said cover layer or said base layer and said cover layer comprising a sample introduction chamber and an optical reading chamber, wherein said optical reading chamber contains a reagent capable of reacting with, wherein said reagent comprises 3-[4,5-dimethylthiazol-2-yl]-2, 5-diphenyltetrazolium bromide.

3. An article suitable for use in determining the concentration of an analyte in a biological sample comprising:
    a multiple-layer element comprising
        (a) a cover layer, said cover layer having a first opening for venting the multiple-layer element and a second opening for receiving a sample of biological fluid; and
        (b) a base layer having a major surface in contact with said cover layer, said base layer or said cover layer or said base layer and said cover layer comprising a sample introduction chamber and an optical reading chamber, further including a colorant for indicating when said optical reading chamber contains an amount of sample sufficient for determining the concentration of an analyte in a biological sample.

4. The article of claim 3, wherein said colorant comprises a dye.

5. The article of claim 4, wherein said dye is selected from the group consisting of Acid Black 2, Acid Black 48, Acid Green 41, Indocyanine Green, Copper Phthalocyaninetetrasulfonic acid, Eriochrome Black T, Gallocyanine, and Janus Green B.

6. The article of claim 3, wherein said colorant is located in said sample introduction chamber.

7. The article of claim 3, wherein said colorant is located in a fluid-transporting layer overlying said sample introduction chamber.

8. The article of claim 3, wherein said colorant is capable of absorbing light at a wavelength of from about 350 nm to about 1400 nm.

9. The article of claim 3, wherein said colorant comprises a pigment.

10. An article suitable for use in determining the concentration of an analyte in a biological simple comprising:
    a multiple-layer element comprising
        (a) a cover layer, said cover layer having a first opening for venting the multiple-layer element and a second opening for receiving a sample of biological fluid; and
        (b) a base layer having a major surface in contact with said cover layer, said base layer or said cover layer or said base layer and said cover layer comprising a sample introduction chamber and an optical reading chamber, wherein said optical reading chamber contains a reagent capable of reacting with the sample, wherein a layer of highly reflective material is located on said cover layer in register with the optical path of said optical reading chamber.

11. The article of claim 10, wherein said layer of highly reflective material becomes less reflective upon being wetted by a liquid sample.

12. The article of claim 10, wherein said layer of highly reflective material is capable of being removed from said optical path by a liquid sample.

13. An article suitable for determining the concentration of an analyte in a biological sample, comprising:

a multiple-layer element comprising:
(a) a base layer
(b) a cover layer, said cover layer having a first opening for venting the multiple-layer element and a second opening for receiving a biological sample; and
(c) a core layer having a first major surface and a second major surface, said core layer disposed between said base layer and said cover layer, said core layer comprising a sample introduction chamber and a optical reading chamber, said first major surface of said core layer in face-to-face contact with said base layer, said second major surface of said core layer in face-to-face contact with said cover layer, wherein said optical reading chamber contains a reagent capable of reacting with glucose, wherein said reagent comprises β-nicotinamide adenine dinucleotide.

14. An article suitable for determining the concentration of an analyte in a biological sample, comprising:
a multiple-layer element comprising:
(a) a base layer
(b) a cover layer, said cover layer having a first opening for venting the multiple-layer element and a second opening for receiving a biological sample; and
(c) a core layer having a first major surface and a second major surface, said core layer disposed between said base layer and said cover layer, said core layer comprising a sample introduction chamber and a optical reading chamber, said first major surface of said core layer in face-to-face contact with said base layer, said second major surface of said core layer in face-to-face contact with said cover layer, wherein said optical reading chamber contains a reagent capable of reacting with glucose, wherein said reagent comprises 3-[4,5-dimethylthiazol-2-yl]-2,5-diphenyltetrazolium bromide.

15. An article suitable for determining the concentration of an analyte in a biological sample, comprising:
a multiple-layer element comprising:
(a) a base layer
(b) a cover layer, said cover layer having a first opening for venting the multiple-layer element and a second opening for receiving a biological sample; and
(c) a core layer having a first major surface and a second major surface, said core layer disposed between said base layer and said cover layer, said core layer comprising a sample introduction chamber and a optical reading chamber, said first major surface of said core layer in face-to-face contact with said base layer, said second major surface of said core layer in face-to-face contact with said cover layer, further including a colorant for indicating when said optical reading chamber contains an amount of sample sufficient for in determining the concentration of an analyte in a biological sample.

16. The article of claim 15, wherein said colorant comprises a dye.

17. The article of claim 16, wherein said dye is selected from the group consisting of Acid Black 2, Acid Black 48, Acid Green 41, Indocyanine Green, Copper Phthalocyanine-tetrasulfonic acid, Eriochrome Black T, Gallocyanine, and Janus Green B.

18. The article of claim 15, wherein said colorant is located in said sample introduction chamber.

19. The article of claim 15, wherein said colorant is located in a fluid-transporting layer overlying said sample introduction chamber.

20. The article of claim 15, wherein said colorant is capable of absorbing light at a wavelength of from about 350 nm to about 1400 nm.

21. The article of claim 15, wherein said colorant comprises a pigment.

22. An article suitable for determining the concentration of an analyte in a biological sample, comprising:
a multiple-layer element comprising:
(a) a base layer
(b) a cover layer, said cover layer having a first opening for venting the multiple-layer element and a second opening for receiving a biological sample; and
(c) a core layer having a first major surface and a second major surface, said core layer disposed between said base layer and said cover layer, said core layer comprising a sample introduction chamber and a optical reading chamber, said first major surface of said core layer in face-to-face contact with said base layer, said second major surface of said core layer in face-to-face contact with said cover layer, wherein a layer of highly reflective material is located on said cover layer in register with the optical path of said optical reading chamber.

23. The article of claim 22, wherein said layer of highly reflective material becomes less reflective upon being wetted by a liquid sample.

24. The article of claim 22, wherein said layer of highly reflective material is capable of being removed from said optical path by a liquid sample.

25. A method for determining the concentration of an analyte in a biological sample, said method comprising the steps of:
(a) introducing a sample of biological fluid obtained from the body of a patient to an article comprising a multiple-layer element having a sample introduction chamber and an optical reading chamber;
(b) allowing a reagent to react with the analyte of interest in the sample; and
(c) measuring the concentration of analyte in the sample by means of an optical instrument, wherein said reagent comprises β-nicotinamide adenine dinucleotide.

26. A method for determining the concentration of an analyte in a biological sample, said method comprising the steps of:
(a) introducing a sample of biological fluid obtained from the body of a patient to an article comprising a multiple-layer element having a sample introduction chamber and an optical reading chamber;
(b) allowing a reagent to react with the analyte of interest in the sample; and
(c) measuring the concentration of analyte in the sample by means of an optical instrument, wherein said reagent comprises 3-[4,5-dimethylthiazol-2-yl]-2,5-diphenyltetrazolium bromide.

27. A method for determining the concentration of an analyte in a biological sample, said method comprising the steps of:
(a) introducing a sample of biological fluid obtained from the body of a patient to an article comprising a multiple-layer element having a sample introduction chamber and an optical reading chamber;
(b) allowing a reagent to react with the analyte of interest in the sample; and
(c) measuring the concentration of analyte in the sample by means of an optical instrument, further including a colorant for indicating when said optical reading chamber contains an amount of sample sufficient for determining the concentration of an analyte in a biological sample.

28. The method of claim 27, wherein said colorant comprises a dye.

29. The method of claim 28, wherein said dye is selected from the group consisting of Acid Black 2, Acid Black 48, Acid Green 41, Indocyanine Green, Copper Phthalocyanine-tetrasulfonic acid, Eriochrome Black T, Gallocyanine, and Janus Green B.

30. The method of claim 27, wherein said colorant is located in said sample introduction chamber.

31. The method of claim 27, wherein said colorant is located in a fluid-transporting layer overlying said sample introduction chamber.

32. The method of claim 27, wherein said colorant is capable of absorbing light at a wavelength of from about 350 nm to about 1400 nm.

33. The method of claim 27, wherein said colorant comprises a pigment.

34. A method for determining the concentration of an analyte in a biological sample, said method comprising the steps of:

(a) introducing a sample of biological fluid obtained from the body of a patient to an article comprising a multiple-layer element having a sample introduction chamber and an optical reading chamber;

(b) allowing a reagent to react with the analyte of interest in the sample; and (c) measuring the concentration of analyte in the sample by means of an optical instrument, wherein a layer of highly reflective material is located on said cover layer in register with the optical path of said optical reading chamber.

35. The method of claim 34, wherein said layer of highly reflective material becomes less reflective upon being wetted by a liquid sample.

36. The method of claim 34, wherein said layer of highly reflective material is removed from said optical path by a liquid sample.

37. The method of claim 34, wherein a change in reflectance in the optical reading chamber indicates that the optical reading chamber contains a sufficient amount of sample to allow an accurate determination of concentration of glucose.

* * * * *

UNITED STATES PATENT AND TRADEMARK OFFICE
CERTIFICATE OF CORRECTION

PATENT NO. : 6,312,888 B1
DATED : November 6, 2001
INVENTOR(S) : Sie Wong et al.

It is certified that error appears in the above-identified patent and that said Letters Patent is hereby corrected as shown below:

Column 24,
Line 10, replace "with" with -- with glucose --
Line 56, replace "the sample" with -- glucose --
Line 45, replace "simple" with -- sample --

Signed and Sealed this

Eighth Day of October, 2002

Attest:

Attesting Officer

JAMES E. ROGAN
Director of the United States Patent and Trademark Office